United States Patent
Leo et al.

(10) Patent No.: US 8,157,789 B2
(45) Date of Patent: Apr. 17, 2012

(54) TOUCH SENSING CATHETER

(75) Inventors: Giovanni Leo, Chene Bougeries (CH); Nicolas Aeby, Geneva (CH); Daniele Inaudi, Lugano (CH)

(73) Assignee: Endosense SA, Meyrin-Geneva (CH)

( * ) Notice: Subject to any disclaimer, the term of this patent is extended or adjusted under 35 U.S.C. 154(b) by 0 days.

(21) Appl. No.: 11/753,429

(22) Filed: May 24, 2007

(65) Prior Publication Data

US 2008/0294144 A1    Nov. 27, 2008

(51) Int. Cl.
*A61M 25/00* (2006.01)
*A61B 1/06* (2006.01)

(52) U.S. Cl. ........................... 604/523; 600/182

(58) Field of Classification Search .................. 604/523, 604/525, 528; 600/141, 145, 182; 385/13
See application file for complete search history.

(56) References Cited

U.S. PATENT DOCUMENTS

| | | | |
|---|---|---|---|
| 4,757,194 A | 7/1988 | Simms |
| 4,873,989 A | 10/1989 | Einzig |
| 4,918,492 A | 4/1990 | Ferdinand et al. |
| 4,966,597 A | 10/1990 | Cosman |
| 4,983,034 A | 1/1991 | Spillman, Jr. |
| 5,014,709 A | 5/1991 | Bjelkhagen et al. |
| 5,018,529 A | 5/1991 | Tenerz et al. |
| 5,065,010 A | 11/1991 | Knute |
| 5,104,392 A | 4/1992 | Kittrell et al. |
| 5,122,137 A | 6/1992 | Lennox |
| 5,178,153 A | 1/1993 | Einzig |
| 5,201,317 A | 4/1993 | Kanazawa et al. |
| 5,202,939 A | 4/1993 | Belleville et al. |
| 5,279,793 A | 1/1994 | Glass |
| 5,289,256 A | 2/1994 | Gramling |
| 5,321,501 A | 6/1994 | Swanson et al. |
| 5,321,510 A | 6/1994 | Childers et al. |

(Continued)

FOREIGN PATENT DOCUMENTS

DE    30 20 785    12/1981

(Continued)

OTHER PUBLICATIONS

Paris-Seely, N.J. et al., "A Compliance-Independent Pressure Transducer for Biomedical Device-Tissue Interfacesm," Biomedical Instrumentation & Technology, Nov.-Dec. 2000, pp. 423-431, vol. 34, No. 6.

(Continued)

*Primary Examiner* — Kevin C Sirmons
*Assistant Examiner* — Bradley Osinski
(74) *Attorney, Agent, or Firm* — Patterson Thuente Christensen Pedersen, P.A.

(57) ABSTRACT

A touch sensing catheter having a strain sensor assembly that may resolve the magnitude and direction of a force exerted on a distal extremity of the catheter, the strain sensor assembly being substantially insensitive to bulk temperature changes. A deformable structure having a plurality of optical fibers associated therewith that are strained by the imposition of a contact force transferred thereto. The optical fibers cooperate with the deformable structure to effect variable gap interferometers, such as Fabry-Perot resonators, that vary in operative length when a force is exerted on the deformable structure. The strain sensor assembly is rendered insensitive to bulk temperature changes by matching the coefficient of thermal expansion of the deformable body with that of the optical fibers. The strain sensor assembly may also be configured to mitigate the effects of thermal gradients using various thermal isolation techniques.

31 Claims, 11 Drawing Sheets

U.S. PATENT DOCUMENTS

| | | | |
|---|---|---|---|
| 5,348,019 A | 9/1994 | Sluss, Jr. et al. | |
| 5,392,117 A | 2/1995 | Belleville et al. | |
| 5,396,887 A | 3/1995 | Imran | |
| 5,409,000 A | 4/1995 | Imran | |
| 5,423,807 A | 6/1995 | Milder | |
| 5,446,546 A | 8/1995 | Breidenbach et al. | |
| 5,575,787 A | 11/1996 | Abela et al. | |
| 5,594,819 A | 1/1997 | Narendran et al. | |
| 5,622,108 A | 4/1997 | Benedetto et al. | |
| 5,633,494 A | 5/1997 | Danisch | |
| 5,645,065 A | 7/1997 | Shapiro et al. | |
| 5,688,267 A | 11/1997 | Panescu et al. | |
| 5,693,043 A | 12/1997 | Kittrell et al. | |
| 5,696,863 A | 12/1997 | Kleinerman | |
| 5,769,847 A | 6/1998 | Panescu et al. | |
| 5,772,590 A | 6/1998 | Webster, Jr. | |
| 5,782,828 A | 7/1998 | Chen et al. | |
| 5,798,521 A | 8/1998 | Froggatt | |
| 5,807,265 A | 9/1998 | Itoigawa et al. | |
| 5,833,688 A | 11/1998 | Sieben et al. | |
| 5,844,927 A | 12/1998 | Kringlebotn | |
| 5,859,717 A * | 1/1999 | Scobey et al. | 398/79 |
| 5,904,658 A | 5/1999 | Niederauer et al. | |
| 5,906,614 A | 5/1999 | Stern et al. | |
| 5,967,978 A | 10/1999 | Littmann et al. | |
| 6,039,743 A | 3/2000 | Quiachon et al. | |
| 6,056,436 A | 5/2000 | Sirkis et al. | |
| 6,063,078 A | 5/2000 | Wittkampf | |
| 6,066,130 A | 5/2000 | Gregory et al. | |
| 6,088,088 A | 7/2000 | Fortenberry | |
| 6,102,926 A | 8/2000 | Tartaglia et al. | |
| 6,113,590 A | 9/2000 | Fischer et al. | |
| 6,113,593 A | 9/2000 | Tu et al. | |
| 6,120,476 A | 9/2000 | Fung et al. | |
| 6,120,520 A | 9/2000 | Saadat et al. | |
| 6,129,667 A | 10/2000 | Dumoulin et al. | |
| 6,133,593 A | 10/2000 | Boos et al. | |
| 6,134,003 A | 10/2000 | Tearney et al. | |
| 6,171,275 B1 | 1/2001 | Webster, Jr. | |
| 6,173,091 B1 | 1/2001 | Reich | |
| 6,175,669 B1 | 1/2001 | Colston et al. | |
| 6,197,023 B1 | 3/2001 | Muntermann | |
| 6,210,346 B1 | 4/2001 | Hall et al. | |
| 6,217,574 B1 | 4/2001 | Webster | |
| 6,226,542 B1 | 5/2001 | Reisfeld | |
| 6,226,551 B1 | 5/2001 | Zhu et al. | |
| 6,246,898 B1 | 6/2001 | Vesely et al. | |
| 6,256,090 B1 | 7/2001 | Chen et al. | |
| 6,262,822 B1 | 7/2001 | Obhi et al. | |
| 6,266,542 B1 | 7/2001 | Stern et al. | |
| 6,266,551 B1 | 7/2001 | Osadchy et al. | |
| 6,272,371 B1 | 8/2001 | Shlomo | |
| 6,276,215 B1 | 8/2001 | Berg | |
| 6,310,990 B1 | 10/2001 | Putnam et al. | |
| 6,324,918 B1 | 12/2001 | Gitis et al. | |
| 6,370,412 B1 | 4/2002 | Armoundas et al. | |
| 6,398,778 B1 | 6/2002 | Gu et al. | |
| 6,425,894 B1 | 7/2002 | Brucker et al. | |
| 6,451,009 B1 | 9/2002 | Dasilva et al. | |
| 6,458,123 B1 | 10/2002 | Brucker et al. | |
| 6,466,811 B1 | 10/2002 | Hassett | |
| 6,470,205 B2 | 10/2002 | Bosselmann et al. | |
| 6,470,286 B1 | 10/2002 | Seip et al. | |
| 6,471,710 B1 | 10/2002 | Bucholtz | |
| 6,546,271 B1 | 4/2003 | Reisfeld | |
| 6,547,780 B1 | 4/2003 | Sinofsky | |
| 6,558,378 B2 | 5/2003 | Sherman et al. | |
| 6,563,970 B1 | 5/2003 | Bohnert et al. | |
| 6,572,804 B2 | 6/2003 | Randall et al. | |
| 6,602,242 B1 | 8/2003 | Fung et al. | |
| 6,660,001 B2 | 12/2003 | Gregory | |
| 6,674,928 B2 | 1/2004 | Johnson et al. | |
| 6,695,808 B2 | 2/2004 | Tom | |
| 6,701,931 B2 | 3/2004 | Sliwa, Jr. et al. | |
| 6,852,109 B2 | 2/2005 | Winston et al. | |
| 6,868,195 B2 | 3/2005 | Fujita | |
| 6,898,338 B2 | 5/2005 | Kersey et al. | |
| 6,915,048 B2 | 7/2005 | Kersey et al. | |
| 6,947,637 B2 | 9/2005 | Smith | |
| 6,955,675 B2 | 10/2005 | Jain | |
| 6,986,769 B2 | 1/2006 | Nelson et al. | |
| 7,004,938 B2 | 2/2006 | Ormsby et al. | |
| 7,050,662 B2 | 5/2006 | Behrmann et al. | |
| 7,173,713 B2 | 2/2007 | Xu et al. | |
| 7,241,986 B2 | 7/2007 | Wang | |
| 7,460,964 B2 | 12/2008 | Mizota et al. | |
| 7,466,879 B2 | 12/2008 | Tjin | |
| 7,491,957 B2 | 2/2009 | Kitamura et al. | |
| 8,048,063 B2 | 11/2011 | Aeby et al. | |
| 8,075,498 B2 | 12/2011 | Leo et al. | |
| 2001/0021843 A1* | 9/2001 | Bosselmann et al. | 606/2 |
| 2002/0041722 A1 | 4/2002 | Johnson et al. | |
| 2002/0041723 A1 | 4/2002 | Ronnekleiv et al. | |
| 2002/0057859 A1 | 5/2002 | Walter et al. | |
| 2002/0072680 A1 | 6/2002 | Schock et al. | |
| 2004/0082844 A1 | 4/2004 | Vardi et al. | |
| 2004/0165810 A1 | 8/2004 | Fujita | |
| 2004/0206365 A1 | 10/2004 | Knowlton | |
| 2004/0243119 A1 | 12/2004 | Lane et al. | |
| 2005/0062979 A1 | 3/2005 | Zhu et al. | |
| 2005/0213870 A1* | 9/2005 | Kersey et al. | 385/13 |
| 2006/0013523 A1 | 1/2006 | Childers et al. | |
| 2006/0045408 A1* | 3/2006 | Jones et al. | 385/12 |
| 2006/0100610 A1 | 5/2006 | Wallace et al. | |
| 2006/0133715 A1 | 6/2006 | Belleville et al. | |
| 2006/0200049 A1 | 9/2006 | Leo et al. | |
| 2006/0263002 A1 | 11/2006 | Pocha et al. | |
| 2007/0014490 A1 | 1/2007 | Silverbrook et al. | |
| 2007/0041019 A1 | 2/2007 | Schmidt | |
| 2007/0043338 A1 | 2/2007 | Moll et al. | |
| 2007/0060847 A1 | 3/2007 | Leo et al. | |
| 2007/0065077 A1 | 3/2007 | Childers et al. | |
| 2007/0151390 A1 | 7/2007 | Blumenkranz et al. | |
| 2007/0151391 A1* | 7/2007 | Larkin et al. | 74/490.06 |
| 2007/0156019 A1 | 7/2007 | Larkin et al. | |
| 2007/0265503 A1 | 11/2007 | Schlesinger et al. | |
| 2008/0009750 A1 | 1/2008 | Aeby et al. | |
| 2008/0294144 A1 | 11/2008 | Leo et al. | |
| 2010/0063478 A1 | 3/2010 | Selkee | |
| 2010/0087835 A1 | 4/2010 | Blumenkranz et al. | |
| 2010/0094163 A1 | 4/2010 | Deladi et al. | |
| 2011/0087112 A1 | 4/2011 | Leo et al. | |

FOREIGN PATENT DOCUMENTS

| | | |
|---|---|---|
| DE | 38 28 550 | 3/1990 |
| EP | 0 281 405 | 9/1988 |
| EP | 0 934 728 A1 | 8/1999 |
| EP | 1909650 | 4/2008 |
| EP | 2047797 | 4/2009 |
| JP | 09297078 | 11/1997 |
| JP | 10137200 A | 5/1998 |
| JP | 2000227367 | 8/2000 |
| JP | 2004251779 | 9/2004 |
| WO | WO9729678 | 8/1997 |
| WO | WO 97/32182 A1 | 9/1997 |
| WO | WO 97/38637 | 10/1997 |
| WO | WO 98/19044 | 5/1998 |
| WO | WO 99/45994 | 9/1999 |
| WO | WO 01/33165 | 5/2001 |
| WO | WO 01/33165 A1 | 5/2001 |
| WO | WO 01/74252 A2 | 10/2001 |
| WO | WO 01/74252 A3 | 10/2001 |
| WO | WO 02/19898 | 3/2002 |
| WO | WO 02/19903 A1 | 3/2002 |
| WO | WO 02/23148 | 3/2002 |
| WO | WO 02/47751 A2 | 6/2002 |
| WO | WO2004/002303 | 1/2004 |
| WO | WO 2004/002303 | 1/2004 |
| WO | WO 2005/059510 A2 | 6/2005 |
| WO | WO 2006/092707 | 9/2006 |
| WO | WO 2007/015139 | 2/2007 |
| WO | WO 2007/015139 A3 | 2/2007 |
| WO | WO 2007/050960 | 5/2007 |
| WO | WO 2007/111737 | 10/2007 |
| WO | WO 2008/000246 | 1/2008 |

| | | | |
|---|---|---|---|
| WO | WO 2008/003307 | 1/2008 | |
| WO | WO 2008/045958 | 4/2008 | |
| WO | WO 2009/114955 | 9/2009 | |

OTHER PUBLICATIONS

Brown, Anthony Wayne, "Deveopment of a Brillouin Scattering Based Distributed Fiber-Optic Strain Sensor," 2001, The University of New Brunswick.
Barrett, M.D. et al., "Extrinsic Fabry-Perot Interometer for Measuring the Stiffness of Ciliary Bundles on Hair Cells," IEEE Transactions on Biomedical Engineering, Mar. 1999, pp. 331-339, vol. 46, No. 3.
Erdemir, A. et al., "Fiberoptic Measurement of Tendon Forces is Influenced by Skin Movement Artifact," Journal of Biomechanics, Mar. 2003, pp. 449-455, vol. 36, No. 3.
Schmidt, Markus et al., "Fiber-Optic Extrinsic Fabry-Perot Interoferometer Strain Sensor with <50 pm Displacement Resolution Using Three-Wavelength Digital Phase Demodulation," Optic Express, Apr. 9, 2001, pp. 475-480, vol. 8, No. 8.
NTT Innovative Technology, "Fiber-Optic Strain-Monitoring Technology: BOTDR (Brillouin Optical Time-Domain Reflectometer)," http://www.ntt-tec.jp/technology/C316.html.
Fearn, I.A. et al., "An Optical Fiber Transducer for Single Myofibril Force Measurement," IEEE Transactions on Biomedical Engineering, Nov. 1993, pp. 1127-1132, vol. 40, No. 11.
Komi, P.V. et al., "Optic Fibre as a Transducer of Tendomuscular Forces," European Journal of Applied Physiology and Occupational Physiology, 1996, pp. 278-280, vol. 72, No. 3.
Del Villar, Ignacio et al., "Optimization of Sensitivity in Long Period Fiber Gratings with Overlay Deposition," Optic Express, Jan. 10, 2005, pp. 56-69, vol. 13, No. 1.
Barb, Matthew et al., "Versatile, High-Speed Force Transducer Using a Laser Diode Beam as an Optical Lever," Journal of Applied Physiology, 2000, pp. 308-314, vol. 88, No. 1.
Rao Y.J., "Recent progress in application of in-fibre Bragg grating sensors," Optics and Lasers in Engineering, Apr. 1999, 31(4): 297-324, Elsevier, UK.
Inaudi, D., "Application of optical fiber sensor in civil structural monitoring," Proceedings of the SPIE—the International Society for Optical Engineering, 2001, pp. 1-7, vol. 4328.
Dupont, "DuPont Zenite LCP liquid crystal polymer resin," Product and Property Guide, K-15415, May 2006.
Park, et al. "Force Sensing Robot Fingers using embedded Fiber Bragg Grating Sensors and Shape Deposition Manufacturing," Center for Design Research, Stanford University, Intelligent Fiber Optic Systems Corporation, Santa Clara, California.
Zhang et al., "On SDM/WDM FBG Sensor Net for Shape Detection of Endoscope," Proceedings of the IEEE International Conference on Mechatronics & Automation Niagara Falls, Canada, Jul. 2005.
U.S. Appl. No. 12/127,657, filed May 27, 2008, Leo.
U.S. Appl. No. 11/989,902, filed Feb. 1, 2008, Leo et al.
U.S. Appl. No. 12/352,426, filed Jan. 12, 2009, Aeby et al.
U.S. Appl. No. 12/152,473, filed May 14, 2008, Leo et al.
Piers, J. et al., "Design of an Optical Force Sensor for Force Feedback furing Minimally Invasive Robotic Surgery," Katholieke Universiteit Leuven, Dept of Mechanical Engineering, Celestijnenlaan.
Yokoyama, MD, et al., "Novel Radiofrequency Ablation Catheter with Contact Force Sensor Predicts Lesion Size and Incidence of Steam Pop in Canine Model," Heart Rhythm Society, May 2007, Denver USA, vol. 4, Issue 5.
Shah et al., "Evaluation of a New Catheter Sensor for Real-Time Measurement of Tissue Contact," Heart Rhythm Society, May 2006, Boston, USA, vol. 3, Issue 5.
"The Unique Force Sensor Ablation Catheter," www.endosense.com/site/product.htm, Mar. 2007.
Xiao, "Fiber Optic Pressure Sensor with Self-Compensation Capability for Harsh Environment Applications," Optical Engineering, vol. 44(5), May 2005.
International Search Report and Written Opinion, dated May 25, 2009.
Endosense receives CE mark for Tacticath force-sensing ablation catheter, May 4, 2009.

Endosense launches TOCCATA clinical study Oct. 7, 2008.
"Endosense achieves ISO 13485 certification" Aug. 12, 2008.
"Endosense unveils five groundbreaking abstracts on contact force measurement for catheter ablation" May 13, 2008.
Fuster et al., "ACC/AHA/ESC 2006 Guidelines for the Management of Patients with Atrial Fibrillation," Circulation Journal of the Americal Heart Association, 2006, Dallas, Texas, pp. e319-e321.
Calkins et al., "HRS/EHRA/ECAS Expert Consensus Statement on Catheter and Surgical Ablation of Atrial Fibrillation: Recommendations for Personnel, Policy, Procedures and Follow-Up," Eurospace (2007.
Natale et al., "Venice Chart Internatinoal Consensus Document on Atrial Fibrillation Ablation," Journal of Cardiovascular Electrophysiology, vol. 18. No. 5, May 2007.
Cappato et al., "Worldwide Survey on the Methdos, Efficacy, and Safety of Catheter Ablation for Human Atrial Fibrillation," Journal of the Americal Heart Association, 2005.
Hasin et al., "Miniature Force Transducer for Myocardial Stimulation and Local Tension Measurements," IEEE Transactions on Biomedical Engineering, vol. BME-26, No. 2, Feb. 1979.
"Sensei X Robotic Catheter System for Electrophysiology Procedures," MedGadget, Sep. 18, 2009.
"Intellisense Fine Force Technology," Hansen Medical (website), http://www.hansenmedical.com/products.intellisense.aspx.
Hansen Medical product brochure, Sensie Robotic Catheter System.
Hansen Medical product brochure, Artisan extend Control Catheter.
Peirs et al., "A micro optical force sensor for force feedback during minimally invasive robotic surgery," Sensors and Actuators A 115 (2004) 447-455.
International Search Report (PCT/IB2009/051967), dated Mar. 16, 2010.
International Search Report (PCT/IB2008/002675), dated Dec. 2, 2009.
Office Action of related application (U.S. Appl. No. 11/237,053), dated Apr. 12, 2010.
Office Action (Restriction Requirement) of related application (U.S. Appl. No. 11/436,926), dated May 22, 2010.
FISO, "FOS-N Strain Sensor," FISO Technologies Inc., (2006), Canada.
Dickmann, "Experiment 03, Fabry Perot Resonator," (2003), pp. 1-19.
Precision Photonics Corporation, "Basic Physics and Design of Etalons," (2003), pp. 1-5.
Luna Innovations, "EFPI Techniques for Strain and Displacement Sensing," (Aug. 1999).
Luna Innovations, "Fiber Optic Bragg Grating Sensor," www.lunainnovations.com/products/shape.asp, (Aug. 2005).
Meller, "Extrinsic Fabry-Perot Interferometer System Using Wavelength Modulated Source," (Dec. 1996).
FISO Technologies, "Technical Note, Principle of Fiber-Optic Sensors," (received prior to Feb. 20, 2007).
Lo, "Using in-fiber Bragg-grating sensors for measuring axial strain and temperature simultaneously on surfaces of structures," Optical Engineering, (Aug. 1998) vol. 37, Issue 8, pp. 2272-2276.
Uffelen, "Anchoring points for fibre optic strain sensors," Optical Techniques for Smart Structures and Structural Monitoring, (Feb. 1997), London, UK.
International Search Report (PCT/IB2010/000021), dated May 27, 2010.
Notification of the First Office Action for Chinese Application No. 20068007106.8 dated May 8, 2009.
Fernandez et al., "Multi-component force sensor based on multiplexed Fibre Bragg grating strain sensors" Measurement Science and Technology (2001) 810-813.
Application and File History for U.S. Appl. No. 11/237,053, filed Sep. 28, 2005, inventor Leo.
European Office Action for European Application No. 06795186.3 dated Nov. 25, 2010.
European Office Action for European Application No. 06710474.5 dated Feb. 16, 2009.
European Office Action for European Application No. 06710474.5 dated Aug. 24, 2009.

Application and File History for U.S. Appl. No. 11/450,072, filed Jun. 9, 2006, inventor Leo.

Application and File History for U.S. Appl. No. 12/352,426, filed Jan. 12, 2009, inventor Leo.

European Office Action from European Application No. 06795186.3 dated Aug. 9, 2011.

European Office Action from European Application No. 11158967.7 dated Aug. 10, 2011.

Notice of Reasons for Rejection (translation) from Japanese Application No. 2007-557615 mailing date: Sep. 13, 2011.

International Preliminary Report on Patentability and Written Opinion from International Application No. PCT/IB2009/051967 date of issuance Nov. 17, 2010.

Application and File History for U.S. Appl. No. 11/237,053, filed Sep. 28, 2005, inventor Leo et al.

Application and File History for U.S. Appl. No. 11/450,072, filed Jun. 9, 2006, inventor Aeby.

Application and File History for U.S. Appl. No. 12/352,426, filed Jan. 12, 2009, inventor Aeby.

Application and File History for U.S. Appl. No. 12/152,473, filed May 14, 2008, inventor Leo.

Application and File History for U.S. Appl. No. 13/096,647, filed Apr. 28, 2011, inventor Leo.

Application and File History for U.S. Appl. No. 13/179,076, filed Jul. 8, 2011.

Application and File History for U.S. Appl. No. 11/436,926, filed May 15, 2006, inventor Leo.

Application and File History for U.S. Appl. No. 11/989,902, filed Feb. 1, 2008, inventor Leo.

* cited by examiner

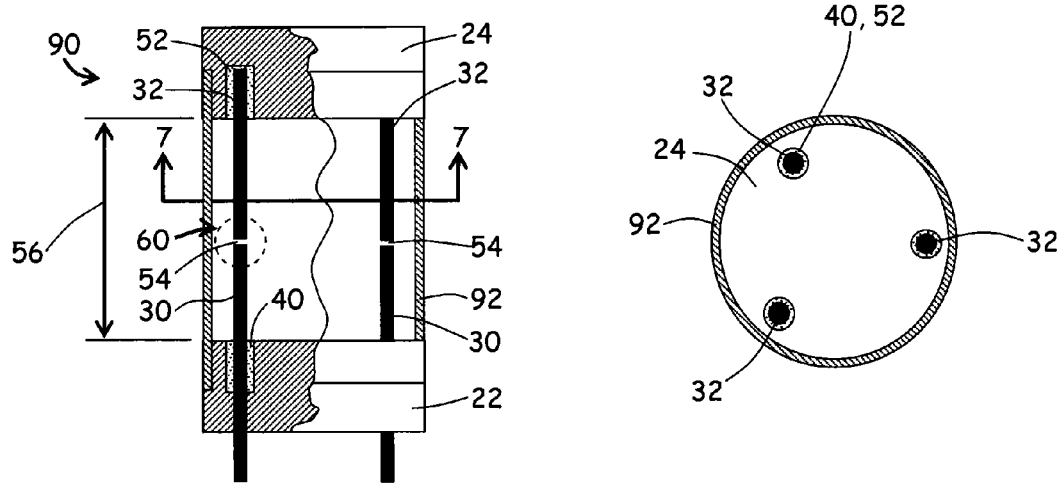
FIG. 6
FIG. 7
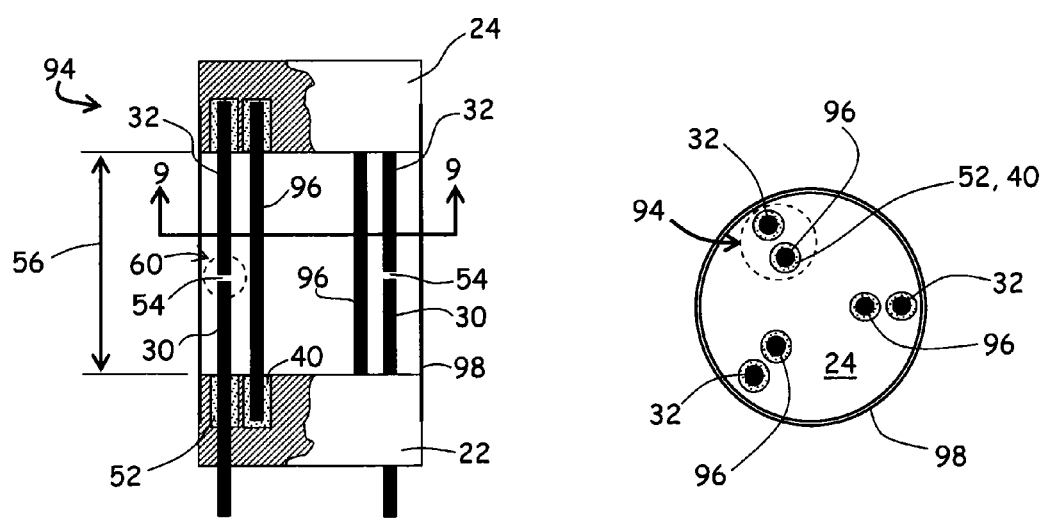
FIG. 8
FIG. 9

TOUCH SENSING CATHETER

FIELD OF THE INVENTION

The disclosed invention relates generally to force sensing devices capable of resolving the magnitude and direction of a force vector. More specifically, the invention relates to a force sensing tip to aid in the positioning of catheters used in humans or animals, or for serving as feedback elements in robotic surgical systems.

BACKGROUND

For many years, exploration and treatment of various organs or vessels has been possible using catheter-based diagnostic and treatment systems. Such catheters are introduced through a vessel leading to the cavity of the organ to be explored or treated or alternatively may be introduced directly through an incision made in the wall of the organ. In this manner, the patient avoids the trauma and extended recuperation times typically associated with open surgical procedures.

To provide effective diagnosis or therapy, it is frequently necessary to first map the zone to be treated with great precision. Such mapping may be performed, for example, when it is desired to selectively ablate current pathways within a heart to treat atrial fibrillation. Often, the mapping procedure is complicated by difficulties in locating the zone(s) to be treated due to periodic movement of the heart throughout the cardiac cycle.

Previously-known systems for mapping the interior of a vessel or organ are described, for example, in U.S. Pat. Nos. 6,546,271 and 6,226,542. The catheters described in those patents employ electromagnetic, electrical, magnetic or acoustic sensors to map the position of a distal end of the catheter in space and then construct a three-dimensional visualization of the vessel or organ interior.

One drawback of such previously known mapping systems is that they rely on manual feedback of the catheter and/or impedance measurements to determine when the catheter is properly positioned in the vessel or organ. Those systems do not measure contact forces with the vessel or organ wall or detect contact forces applied by the catheter against the organ or vessel wall that may modify the true wall location. Instead, previously known mapping methods are time-consuming, dependent upon the skill of the clinician, and cannot compensate for artifacts created by excessive contact forces.

It therefore would be desirable to provide apparatus and methods for detecting and monitoring contact forces between a mapping catheter and the wall of the organ or vessel to permit faster and more accurate mapping. It also would be desirable to provide apparatus and methods that permit the process to be automated.

Once the topography of the vessel or organ is mapped, either the same or a different catheter may be employed to effect treatment. Depending upon the specific treatment to be applied to the vessel or organ, the catheter may comprise any of a number of end effectors, such as but not limited to RF ablation electrodes, rotary or scissor action cutting heads, laser ablation system, injection or sewing needles, fluid conveyance systems, forceps, manipulators, mapping electrodes, endoscopic vision systems and therapeutic delivery systems such as genetic impregnation devices. Exemplary systems are described, for example, in U.S. Pat. Nos. 6,120,520, 6,102,926, 5,575,787, 5,409,000 and 5,423,807.

The effectiveness of such end effectors often depends on having the end effector in contact with the tissue of the wall of the organ or vessel. Many previously-known treatment systems include expandable baskets or hooks that stabilize the distal extremity of the catheter in contact with the tissue. Such arrangements, however, may be inherently imprecise due to the motion of the organ or vessel. Moreover, the previously-known systems do not provide the ability to sense the load applied to the distal extremity of the catheter by movement of the tissue wall.

For example, in the case of a cardiac ablation system, at one extreme the creation of a gap between the end effector of the treatment system and the tissue wall may render the treatment ineffective, and inadequately ablate the tissue zone. At the other extreme, if the end effector of the catheter contacts the tissue wall with excessive force, it may inadvertently puncture the tissue, resulting in cardiac tamponade.

In view of the foregoing, it would be desirable to provide a catheter-based diagnostic or treatment system that permits sensing of the load applied to the distal extremity of the catheter, including periodic loads arising from movement of the organ or tissue. It further would be desirable to have a load sensing system coupled to control operation of the end effector, so that the end effector is operated, either manually or automatically, only when the contact force is detected to fall within a predetermined range.

U.S. Pat. No. 6,695,808 proposes several solutions to measure the force vector arising from contact with the tissue surface, including mechanical, capacitive, inductive and resistive pressure sensing devices. One drawback of such devices, however, is that they are relatively complex and must be sealed to prevent blood or other liquids from disturbing the measurements. In addition, such load sensing devices may result in an increase in the insertion profile of the distal extremity of the catheter. Still further, sensors of the types described in that patent may be subject to electromagnetic interference.

One previously-known solution for dealing with potential electromagnetic interference in the medical environment is to use light-based systems rather than electrical measurement systems. One such light-based system is described in U.S. Pat. No. 6,470,205 to Bosselman which describes a robotic system for performing surgery comprising a series of rigid links coupled by articulated joints. A plurality of Bragg gratings are disposed at the articulated joints so that the bend angle of each joint may be determined optically, for example, by measuring the change in the wavelength of light reflected by the Bragg gratings using an interferometer.

International Publication No. WO 01/33165 to Bucholtz describes an alternative spatial orientation system wherein wavelength changes measured in a triad of optical fiber strain sensors are used to compute the spatial orientation of a catheter or other medical instrument. Although Bucholtz discloses that the strain sensors may be encased within a deformable sheath, as is also described in Bosselman, calculation of the bend angles is not described as requiring characterization of the material properties of the deformable sheath.

Accordingly, it would be desirable to provide diagnostic and treatment apparatus, such as a catheter or guide wire, that permits sensing of loads applied to a distal extremity of the apparatus, but which do not substantially increase the insertion profile of the apparatus. It is further desirable to provide diagnostic and treatment apparatus, such as a catheter and guide wire, that permits computation of forces applied to a distal extremity of the apparatus, and which are substantially immune to electromagnetic interference.

An article by J. Peirs et al., entitled "Design of an Optical Force Sensor for Force Feedback during Minimally Invasive Robotic Surgery," published by Katholieke Universiteit Leuven, Belgium, describes a tri-axial force sensor for use generating force feedback systems in a robotic surgery system. The apparatus includes a plurality of optical fibers that direct light onto a mirrored surface disposed adjacent to a distal tip of the device. The intensity of the light reflected from the mirrored surface is measured and may be correlated to the force required to impose a predetermined amount of flexure to the distal tip. The article describes a flexible and compact structure that may be used to produce variations in light intensity responsive to contact forces that deform the structure.

International Publication No. WO 2007/015139 to Leo, et al. (Leo), discloses a device and method for resolving a force vector (magnitude and direction) applied to the distal end of a catheter. Leo discloses the use of fiber optic strain elements in a catheter that maintains essentially the same profile as with catheters that do not sense touching forces and is substantially immune to electromagnetic interference.

Temperature changes to the probe of Leo may cause the strain elements to expand or contract relative to a reference or null state and present a false indication of mechanical strain on the elements. Accordingly, Leo discloses the use of additional fiber optic strain elements that are not subject to a mechanical load to provide an indication of the effect of the bulk temperature change of the probe, such as the shift in the returned wavelength of a fiber Bragg grating. Leo also discloses the use of temperature sensors disposed in the distal end of the probe to enable compensation of deformations arising from temperature variations.

While the catheter with fiber optic strain elements in Leo may be useful in certain medical procedures, a limitation to the temperature indication techniques disclosed above is that the sensors are influenced by a temperature at a location that is physically removed from the strain sensing elements that resolve the force vector. The temperature compensation sensors disclosed above cannot be mounted in direct contact with the fiber optic sensor because they will interfere with the operation of and/or create a random error in the strain indications. Additional limitations of certain temperature compensation techniques may include added stiffness of the sensing structure (e.g. thermocouples), an increased profile of the catheter, or an increase in the complexity of the assembly.

The above-mentioned references also do not disclose ways to mitigate the effects of thermal gradients within the sensor tip. Thermal gradients differ from bulk temperature changes in that they produce a range of temperatures that are present simultaneously within an assembly, even when the assembly is in thermal equilibrium. Thermal gradients commonly occur in catheter assemblies that deliver energy to a target area, such as RF ablation electrodes. The end effectors in these systems may require, for example, the delivery of an irrigation fluid that is substantially cooler than the surrounding blood temperature in order to effectively cool the end effector. The catheter and force sensing assembly contained therein may therefore be in contact with both warmer and cooler components relative to the surrounding (body fluid) temperature, causing the temperature of the force sensing assembly to be non-uniform, even when the catheter is at thermal equilibrium.

It is therefore desirable is to provide a diagnostic and treatment apparatus, such as a catheter system, that permits computation of forces applied to a distal extremity of the catheter and is substantially insensitive to the thermal environment encountered during use of the catheter, such as exposure to body fluids and the presence of room-to-body temperature gradients, delivery of energy by an end effector and other sources of thermal gradients.

SUMMARY OF THE DISCLOSURE

Various embodiments of the invention largely counter the effects of bulk temperature change on the strain elements of a force sensor suitable for use in a low profile assembly, such as a catheter. In various embodiments, a catheter comprising a flexible elongated body includes a strain sensor assembly affixed thereto. The strain sensor assembly includes a deformable structure having a plurality of optical fibers associated therewith. The deformable structure is strained by the imposition of a contact force transferred to the strain sensor assembly. The optical fibers are disposed relative to the deformable structure to create interferometric gaps that vary in operative length resulting from longitudinal and radial deformations of the deformable structure. Changes in the operative lengths in turn produce changes to interferometric patterns that are returned by the interferometric gaps when they are interrogated by an electromagnetic source. A controller may be provided to compute a force vector responsive to the changes in the detected interferometric pattern.

Certain embodiments also moderate the effects of temperature gradients within a sensor assembly. Furthermore, embodiments of the invention may be configured to provide substantial mechanical amplification of the strain relative to the deflected portion of the optical assembly. In various embodiments, the above is accomplished without substantial increase to the profile of standard sized catheters, such as RF ablative head catheters. The resolution of the force vector may exceed 1-gm, a significant improvement over current fiber optic based sensors which can experience bias errors exceeding 10-gm per Kelvin of temperature change. The three-dimensional directional angle may be determined to within 5 angular degrees accuracy, and in many cases to within 1 angular degree.

In some embodiments, the strain induced on a deflectable structure is detected with fiber optic sensors that operate on an interferometeric gap principle. With so-called "gap interferometers," an interference pattern is created between electromagnetic energy reflected from a first reflecting surface and electromagnetic energy reflected from a second reflecting surface, the second reflecting surface being separated from the first reflecting surface. Gap interferometers that operate on this principle include but are not limited to Michelson interferometers, intrinsic Fabry-Perot resonators (where the Fabry-Perot cavity is internal to a fiber optic) and extrinsic Fabry-Perot resonators (where the Fabry-Perot cavity is external to a fiber optic). The frequency of the interference pattern is a function of several parameters, including a distance or "operative length" between the first and second reflecting surfaces, which is designed to change in proportion to the strain induced within the deflectable structure in response to an external force applied thereto. Interferometric techniques utilizing laser sources can provide an indication of the change of the distance between the reflecting surfaces. Techniques utilizing white light sources may also be implemented, providing an indication of the actual gap dimension.

Embodiments are disclosed that substantially remedy the effects of thermal expansion. The gap that defines the interferometer is maintained between a transmitting element and a reflector element, each being supported by or being integral with portions of a deflectable structure having opposed faces that generally face each other. The distance between the opposed faces of the deflectable structure is maintained by a standoff member or members. The standoff member(s) and the transmitting member may be made of materials having coefficients of thermal expansion (CTEs) that are substantially similar. Hence, as the standoff member expands or contracts with temperature change, the transmitting element will undergo generally the same expansion or contraction to maintain the gap at substantially the same dimension. In this way, the gap dimension of the interferometer is largely insensitive to bulk temperature change of the standoff and transmitting element while remaining sensitive to changes induced by deformation of the deflectable structure.

The dimension of the interferometric gap may be maintained in other embodiments by a structure that is designed to mechanically amplify the change in the gap dimension when a force is applied or transferred to the deflectable structure. The mechanical amplification may be achieved by incorporation of a standoff member or members that control the dimension of the gap while establishing an active length that is substantially longer than the dimension of the gap. The change in the dimension of the gap is proportional to the accumulated strain across the active length of the standoff member(s) to provide the amplification.

Still other embodiments incorporate designs that reduce potential temperature gradients within the strains sensor assembly. Such designs may utilize various gaps between portions of the deflectable sensor that represent temperature extremes within the strain sensor assembly. The combination of mitigated temperature gradients and low CTEs of the deflectable structure (e.g. 0.5- to 2.0-$\times 10^{-6}$ per Kelvin) cooperate produce changes in the gap dimension that may be undetectable or tolerably small in operation.

In one embodiment, a deflectable structure having proximal portion and a distal portion separated by at least one standoff member defines a separation between the proximal portion and the distal portion. A plurality of transmitting elements extending from the proximal portion and partially span the separation, each of the plurality of transmitting elements including a free end to define a plurality of free ends located between the proximal portion and the distal portion. At least one reflecting element is operatively coupled with the plurality of free ends for forming a plurality of gap interferometers, such as Fabry-Perot resonators, one of the plurality of interferometers being presented between each of the plurality of free ends and the at least one reflecting element, with each of the plurality of interferometers having an operative length between the respective free end and the at least one reflecting element. The operative length is variable and responsive to deformation of the deflectable structure. The at least one standoff portion and the transmitting element may include a substantially similar coefficient of thermal expansion in a direction parallel to the operative lengths of the plurality of interferometers so that the operative length remains within a predetermined range when the deformable structure is subject to a predetermined temperature change.

Certain embodiments may implement a configuration for amplifying the displacement of a interferometric gap fiber optic strain gage by attaching a standoff member to a deformable assembly at two locations with a span length between the locations. An optical fiber extending substantially parallel to the standoff is attached to the standoff member and includes a free end that is partially reflective. In this embodiment, a reflector faces the free end with a variable gap therebetween, with the reflector, free end and variable gap defining an interferometric gap. The variable gap is varied when the standoff is subjected to a mechanical strain.

The various embodiments may also include a source of electromagnetic radiation operatively coupled to and transmitting electromagnetic radiation through each of the plurality of transmitting elements to form the plurality of interferometric gaps. Each of the interferometric gaps outputs a modulated waveform characteristic of the corresponding of the operative lengths. A receiver may be operatively coupled to the plurality of transmitting elements to detect the modulated waveform.

In another embodiment, a catheter for use in a medical procedure incorporates a flexible elongate body adopted to be introduced into a patient during the medical procedure and including a strain sensing assembly proximate a deformable portion of the elongate body. The strain sensing assembly includes a proximal portion and a distal portion separated by at least one standoff member to define a separation between the proximal portion and the distal portion. A plurality of transmitting elements extend from the proximal portion and partially spans the separation. Each of the plurality of transmitting elements includes a free end to define a plurality of free ends located between the proximal portion and the distal portion. At least one reflecting element is operatively coupled with at least one of the plurality of free ends to define a plurality of gaps for interferometery (one of the plurality of gaps being presented between each of the plurality of free ends and the at least one reflecting element). Each of the plurality of gaps has an operative length between the respective free end and the at least one reflecting element, the operative length being variable and responsive to deformation of the deformable portion of the elongate body. The at least one standoff portion and the transmitting element includes a substantially similar coefficient of thermal expansion in a direction parallel to the operative lengths of the plurality of gaps so that each of the operative lengths remains within a predetermined range when the deformable portion of the elongate body is subject to a predetermined range of bulk temperature change.

An embodiment of the invention wherein the displacement of a fiber optic strain gage is mechanically amplified is also presented. A standoff member is attached to a deformable structure at two locations with a span length between the locations. An optical transmitting element extends substantially parallel to the standoff member along the span length, the optical transmitting element being attached to the standoff member and including a free end that is partially reflective. The optical transmitting element has a coefficient of thermal expansion substantially similar to the optical transmitting element. A reflector faces the free end to define an interferometric gap therebetween, the interferometric gap having an operative length. The operative length of the interferometric gap is varied when the standoff member is subjected to a mechanical strain for operation of the interferometric gap as the fiber optic strain gauge.

In yet another embodiment, a strain sensor assembly includes a deformable structure and a plurality of gap interferometers operably coupled with the deformable structure. Each of the plurality of gap interferometers includes a transmitting element and also has an operative length that varies when the deformable structure is subjected to an external force. The transmitting element and the deformable structure are constructed from materials having similar coefficients of thermal expansion that enables the operative length to remain within a predetermined range when the deformable structure is subject to a predetermined range of bulk temperature change.

In another embodiment of the invention, method of making a strain sensor assembly is disclosed. The method includes selecting at least one transmitting element having a first coefficient of thermal expansion and fabricating a deformable structure including at least one standoff member, each of the at least one standoff member having a second coefficient of thermal expansion that is substantially similar to the first coefficient of thermal expansion. The method may also include attaching the transmitting element to the deformable structure to provide an active length of the strain sensor assembly.

In yet another embodiment of the invention, a method of making a strain sensor assembly includes selecting a strain sensing element including a transmitting element coaxial with a standoff member, the transmitting element and the standoff member having a substantially similar first coefficient of thermal expansion. The method also includes fabricating a deformable structure having a second coefficient of thermal expansion that is substantially similar to the first coefficient of thermal expansion and attaching the strain sensing element to the deformable structure to provide an active length.

In another embodiment, a force sensing catheter assembly is disclosed including a deformable structure having a first coefficient of thermal expansion and a plurality of strain sensing elements operatively coupled with the deformable structure. Each of the plurality of strain sensing elements includes a transmitting element and a reflecting element coaxial with and attached to a standoff member to form a gap having an operative length between the transmitting element and the reflecting element. The transmitting element, the reflecting element and the standoff member each have a coefficient of thermal expansion substantially similar to the first coefficient of thermal expansion.

In still another embodiment, a device for introduction into a human or animal body is disclosed and includes a flexible elongate body adapted to traverse a body passageway, the elongate body having a distal extremity for contact with a tissue wall of a vessel or organ. A deformable body is operatively coupled with the flexible elongate body that deforms in response to a contact force generated between the distal extremity and the tissue wall of the vessel or organ. The deformable body has a first coefficient of thermal expansion. A plurality of optical fiber sensors, each responsive to the contact force, the has a second coefficient of thermal expansion substantially similar to the first coefficient of thermal expansion such that an indication of the contact force is generated by each of the optical fiber sensors when sourced with electromagnetic radiation. The indication of the contact force is relatively insensitive to temperature over an operating range of temperatures of at least 5° C.

BRIEF DESCRIPTION OF THE DRAWINGS

FIG. 6 is an enlarged cutaway view of a strain sensor assembly according to an embodiment of the invention;

FIG. 7 is a sectional view of the strain sensor assembly of FIG. 6;

FIG. 8 is an enlarged cutaway view of a strain sensor assembly according to an embodiment of the invention;

FIG. 9 is a sectional view of the strain sensor assembly of FIG. 8;

DETAILED DESCRIPTION

Figure 1:
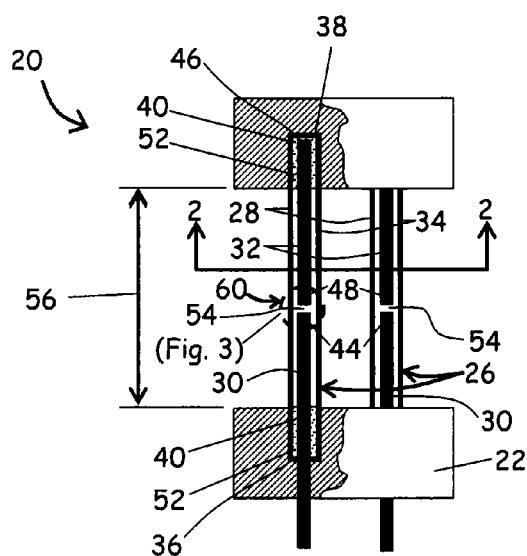
FIG. 1 is an enlarged cutaway view of a strain sensor assembly according to an embodiment of the invention.
Figure 2:
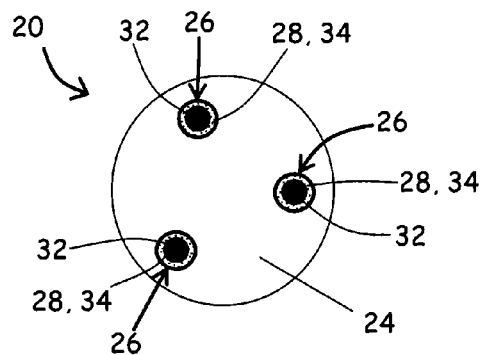
FIG. 2 is a sectional view of the strain sensor assembly of FIG. 1.
Figure 3:
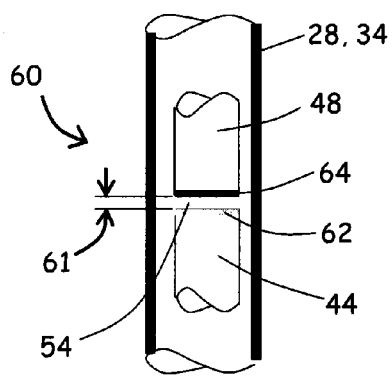
FIG. 3 is an expanded view of the interferometric gap of FIGS. 1 and 4.

Referring to FIGS. 1 through 3, a strain sensor assembly 20 is depicted according to an embodiment of the invention. In this embodiment, a proximal or base portion 22 and a distal or head portion 24 are separated by a trio of strain sensing elements 26. Each strain sensing element 26 includes the standoff member 28, a transmitting element 30 and a reflecting element 32. Each standoff member 28 is comprised of a hollow tube 34 having a proximal end 36 and a distal end 38 that are disposed in sockets 40 formed in the proximal and distal portions 22 and 24.

In this embodiment, the transmitting element 30 of each strain sensing element 26 includes a free end 44 that extends partway into the hollow tube 34. The reflecting element 32 includes an anchor end 46 and a free end 48 and is housed within the hollow tube 34 opposite the transmitting element 30.

The transmitting and reflecting elements 38 and 42 are each secured to the hollow tube 36 with a potting 52 and are positioned to define a gap 54 between the free ends 44 and 48. Each of the strain sensing elements 26 are characterized by an active or strain sensing length 56 that is defined by the distance between the pottings 52.

The gap 54 and the free ends 44 and 48 of the transmitting and reflecting elements 30 and 32 may cooperate to define an interferometric gap 60 having an operative length 61. The operative length 61 is the distance that establishes the characteristics of the interference pattern reflected back from the interferometric gap 60. Accordingly, the free end 44 of the transmitting element 30 may be faced with a semi-reflecting surface 62, and the free end 48 of the reflecting element 32 may be faced with a reflecting surface 64.

An "interferometric gap" as used herein is a gap having the qualities of the cavity of an interferometer, such as found in a Michelson interferometer or a Fabry-Perot resonator. Likewise, a "gap interferometer" as used herein is an interferometer that utilizes an interferometric gap to produce an interference pattern.

The proximal and distal ends 28 and 32 may be press fit, glued or formed integrally with the respective proximal and distal portions 22 and 24. The pottings 52 may be comprised of a glue, epoxy or other adhesive compatible with the application and available to the artisan.

Figure 4:
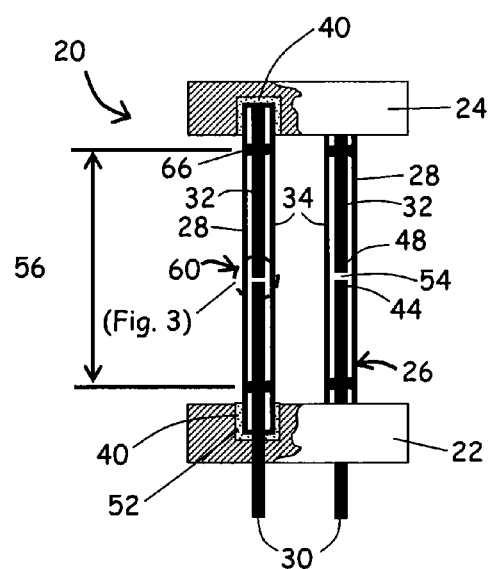
FIG. 4 is an enlarged cutaway view of a strain sensor assembly according to an embodiment of the invention.

Referring to FIG. 4, an alternative embodiment of the strain sensor assembly 20 is depicted. In this embodiment, the proximal and distal ends 36 and 38 of the standoff members 28 are attached to the proximal and distal portions 22 and 24 of the strain sensor assembly 20 with potting 52. However, the transmitting and reflecting elements 30 and 32 are each connected to the hollow tube 34 with a fusion weld 66. For reasons discussed in connection with FIGS. 20C and 20D, the separation between the fusion welds 66 defines the active length 56 of the strain sensing element 26 in the embodiment of FIG. 4.

In the preceding embodiments, the hollow tube 34, transmitting element 30 and reflecting element 32 may be constructed of the same material, such as quartz. The proximal and distal portions 22 and 24 may also be constructed from the same material, or of a material having a similar coefficient of thermal expansion (CTE). Likewise, the potting 52 may be chosen for a closely matching CTE.

Another factor is the moisture retention or hygroscopicity of the materials that comprise the strain sensor assembly 20. Hygroscopic materials absorb moisture and may tend to grow or swell when immersed in a liquid medium. The effect on the strain sensing elements 26 differ from the effects of thermal expansion in that only those elements exposed to the liquid medium (i.e. the hollow tube 34) are potentially subject to dimensional change. In this scenario, the hollow tube 34, which defines active length 56, may undergo a dimensional change, whereas the transmitting and reflecting elements 30 and 32 contained therein and isolated from the moisture would not undergo a proportional dimensional change.

However, certain fiber optic materials, such as quartz, are known to be substantially non-absorbent and do not undergo detectable dimensional changes of significance when exposed to moisture.

Figure 5:
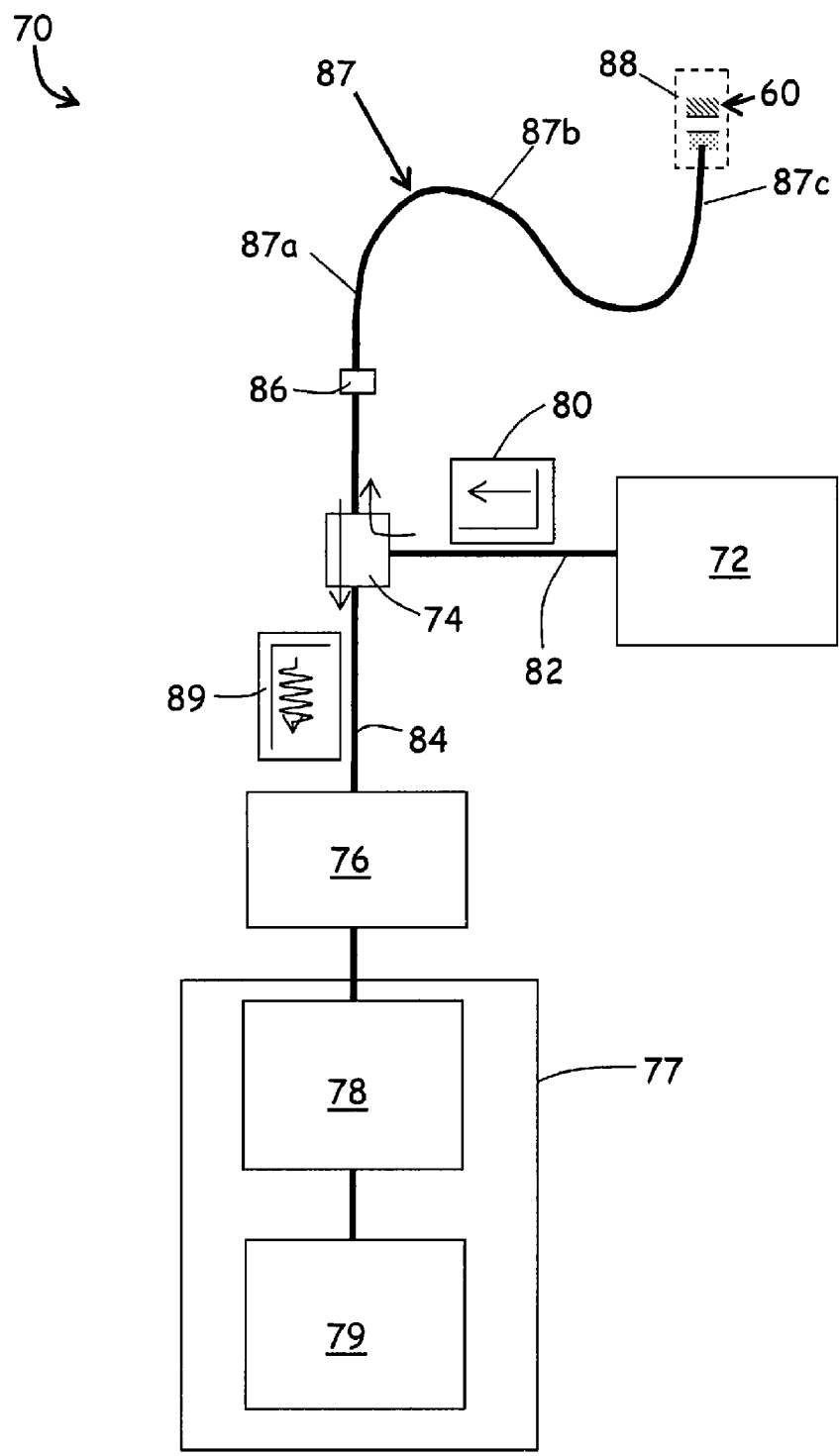
FIG. 5 is a block diagram of a strain sensing system in an embodiment of the invention.

Referring to FIG. 5, an embodiment of a strain sensing system 70 is depicted in accordance with the invention. The strain sensing system 70 may comprise an electromagnetic source 72, a coupler 74, a receiver 76, an operator console 77 operatively coupled with a microprocessor 78 and a storage device 79. The electromagnetic source 72 outputs a transmitted radiation 80 of electromagnetic radiation that is substantially steady state in nature, such as a laser or a broadband light source. A transmission line 82 such as a fiber optic cable carries the transmitted radiation 80 to the coupler 74, which directs the transmitted radiation 80 through a transmitting/receiving line 84 to the transmitting element 30. A portion of the transmitted radiation 80 enters the interferometric gap 60 within the strain sensing element 26. The transmitting element 30 and transmitting/receiving line 84 may be coupled through a connector 86 as depicted in FIG. 5.

The transmitting/receiving line 84 may be operatively coupled with the interferometric gap 60 through a flexible, elongate catheter assembly 87. In one embodiment, the catheter assembly 87 comprises a proximal portion 87a, a middle portion 87b and a distal portion 87c. The distal portion 87c may include an end effector 88 that contains the interferometric gap 60. The catheter assembly may be of a hollow construction (i.e. having a lumen) or of a non-hollow construction (i.e. no lumen), depending on the application.

A portion of the radiation that enters the interferometric gap 60 is returned to transmitting element 30 as a modulated waveform 89 and is transmitted back through the transmitting/receiving line 84 to the receiver 76. The strain sensing system 70 may interrogate the interferometric gap 60 at an exemplary and non-limiting rate of 10-Hz. The receiver 76 may be chosen from a variety of receiving devices available in the art, such as but not limited to that disclosed in U.S. Pat. Nos. 5,202,939 and 5,392,117 to Belleville, et al., disclosures of which are hereby incorporated by reference other than any express definitions of terms specifically defined therein. The receiver 76 manipulates and/or converts the incoming modulated waveform 89 into digital signals for processing by the microprocessor 78.

In operation, the characteristics of the modulated waveform 89 are determined in part by the dimension of the gap 54. The strain sensor assembly 20 is configured so that the gap 54 will vary when the strain sensing element 26, or more specifically the standoff member 28, experiences an axial strain. A change in the axial strain will cause a proportional change in the dimension of the gap 54, thereby altering the characteristic of the modulated waveform 89 transmitted to the receiver 76.

The preceding embodiments provide a mechanical amplification of the growth of the gap 54 relative to the strain experienced by the strain sensing elements 26. The gap 54 is maintained by the locations where the transmitting and reflecting elements 30 and 32 is anchored to the standoff members 28 (i.e. pottings 52 or fusion welds 66). Accordingly, the gap 54 will be displaced by an accumulated change in the active length 56 due to axial loading (tension or compression). The construction of the strain sensing elements 26 may be such that the active length 56 is several hundred times greater than the gap 54, which provides substantial amplification of the gap 54 relative to its dimension.

Where the standoff members 28, transmitting element 30 and reflecting element 32 are constructed of the same material, the preceding embodiments may also be relatively insensitive to bulk temperature changes of the strain sensor assembly 20. For the embodiments depicted in FIGS. 1 through 4, a change in the length $\Delta L_S$ of the standoff member 28 across the active length 56 of the strain sensing element 26 is expressed by $$\Delta L_S = [\alpha \cdot L \cdot \Delta T]_S \qquad \text{Eqn. (1)}$$

where L, $\alpha$ and $\Delta T$ are, respectively, the CTE, length and the change in the bulk temperature, and the subscript "S" denotes the standoff member 28. Likewise, the changes in the lengths $\Delta L_T$ and $\Delta L_R$ of the transmitting and reflecting members 30 and 32 across the active length 56 of the strain sensing element 26 are expressed by $$\Delta L_T = [\alpha \cdot L \cdot \Delta T]_T \qquad \text{Eqn. (2)}$$

$$\Delta L_R = [\alpha \cdot L \cdot \Delta T]_R \qquad \text{Eqn. (3)}$$

where the subscripts "T" and "R" denote, respectively, the transmitting element 30 and the reflecting element 32. Also, as depicted in FIGS. 1 and 3, the operative length 61 of the interferometric gap 60 can be expressed in terms of the lengths $L_S$, $L_T$ and $L_R$ as follows:

$$l_G = L_S - (L_T + L_R) \qquad \text{Eqn. (4)}$$

where $l_G$ is the operative length 61 of the interferometric gap 60. Accordingly, the change in the length $\Delta l_G$ may be expressed by $$\Delta l_G = \Delta L_S - (\Delta L_T + \Delta L_R) = [\alpha \cdot L \cdot \Delta T]_S - ([\alpha \cdot L \cdot \Delta T]_T + [\alpha \cdot L \cdot \Delta T]_R) \qquad \text{Eqn. (5)}$$

Consider a scenario where change in the bulk temperature of the strain sensor assembly 20 is uniform, i.e. $\Delta T_S = \Delta T_T = \Delta T_R = \Delta T$. Consider further the scenario where the CTE of the various components are equal, i.e. $\alpha_S = \alpha_T = \alpha_R = \alpha$. The expression of Eqn. 5 then reduces to $$\Delta l_G = \alpha \cdot \Delta T \cdot [L_S - (L_T + L_R)] = \alpha \cdot \Delta T \cdot l_G \qquad \text{Eqn. (6)}$$

Hence, for configurations such as depicted in FIGS. 1 through 4 that incorporate standoff members 28, transmitting elements 30 and reflecting elements 32 that are constructed of the same material or materials having substantially the same CTE, the accumulated change in the active length 56 may dominate the change in the dimension of the gap 54 by a factor of several hundred times, making the assembly relatively insensitive to bulk temperature changes.

Also, for strain sensor assemblies 20 that utilize materials of low hygroscopicity, the change in the active length 56 of the strain sensing element 26 may be negligible when exposed to fluids. Alternatively, some or all of the components of the strain sensor assembly 20 may be plated or coated with a material that serves as a barrier to moisture such as poly-para-xylylene (PARYLENE). Accordingly, the embodiments depicted in FIG. 1 and FIG. 4 may be made insensitive to moisture as well as bulk temperature change by proper selection of fabrication materials.

Referring to FIGS. 6 and 7, a strain sensor assembly 90 is presented as an alternative to the strain sensor assembly 20 wherein the transmitting and reflecting elements 30, 32 are housed within in a single support tube 92. The single support tube 92 replaces the multiple hollow tubes 34 of FIGS. 1 through 4 and maintains the active length 56 of the strain sensor assembly 20. The proximal and distal end portions 22 and 24 are glued to the open ends of the single support tube 92 to form an enclosure. Alternatively, the support tube 92 may be mounted in ring-shaped grooves formed on the interior faces of the proximal and distal end portions 22, 24 (not depicted).

Referring to FIGS. 7 and 8, a strain sensor assembly 94 is depicted in another embodiment of the invention wherein the strain sensing elements 94 each comprise a standoff member 28 that is adjacent to rather than concentric with the transmitting and reflecting elements 30 and 32. The standoff member 28 may take the form of a straight, cylindrical rod 96 as depicted, or other shapes and cross sections. A thin tubular membrane 98 may shroud the active length 56 of the strain sensor assembly 94 to encapsulate the sensing elements 26 in a common closure.

Functionally, the tubular membrane 98 acts to keep body fluid from flooding the gap 54 and interfering with the operation of the interferometric gap 60. The configuration and arrangement of the tubular membrane 98 may be such that it does not exert a detectable force on the strain sensor assembly 94 when subject to thermal expansion or contraction. For example, the tubular membrane 98 may be of such a thin wall and of a compliant material so that it offers negligible resistance to compression, such as with a latex or rubber material. Also, the tubular membrane 98 may be mounted to the strain sensor assembly 94 with an excess length to enable the assembly to grow or contract and the gasses trapped within the annular gap 54 to expand or contract without exerting a tension force on the strain sensor assembly.

The strain sensor assembly 94 also reduces the potential deformation and attendant effect on the dimension of the gap 54 that may be caused by the expansion of trapped gas in the strain sensor elements 26 used in the strain sensor assembly 20. Generally, the effects of trapped gas on a strain measurement may be secondary or insignificant, and may not warrant attention. However, there may be applications where the expansion or contraction of trapped gas within a strain sensor assembly is notable vis-à-vis the accuracy or resolution requirements of the application.

Pneumatically, the hollow tubes 34 of the sensor elements 26 each represent a thin-walled cylindrical vessel with a large length-to-diameter or "aspect" ratio. The pressure of the gas entrapped within the sensor element 26 will increase or decrease with temperature change, and may cause the profile of the hollow tube 34 to bulge or flex outward when the gas expands or inward when the gas contracts. The expansion or contraction may also impose an axial strain on the hollow tube 34.

Unlike the effect caused by the CTE of the sensor components, there is no congruent and offsetting expansion of the transmitting and reflecting elements 30 and 32. Hence, the combination of flexure of the wall and the axial strain of the hollow tube 34 may cause the dimension of the gap 54 to change and cause the strains sensing system 70 to register a false change in the resolved force vector.

Likewise, the strain sensor assembly 90 of FIGS. 6 and 7 also include a volume of trapped gas that generally may cause deformation of the structure (i.e. single support tube 92) that maintains the gap 54. The configuration of strain sensor assembly 90 will also generally be more rigid and less sensitive to applied forces than the configuration of strain sensor assembly 20.

The strain sensor assembly 94 reduces these deleterious effects because expansion of the trapped gas does act principally on the structure that also maintains the gap 54. Rather, the pressure change will act primarily on the tubular membrane 98, which is not a support element. The tubular membrane 98 may be dimensioned to freely flex inward and outward, thereby greatly reducing the pressure change and the attendant axial strain imposed on the rod members 96. The rod members 96 may be sized to provide substantially less cross-sectional area and less stiffness than the single support tube 92 of strain sensor assembly 90.

Figure 10:
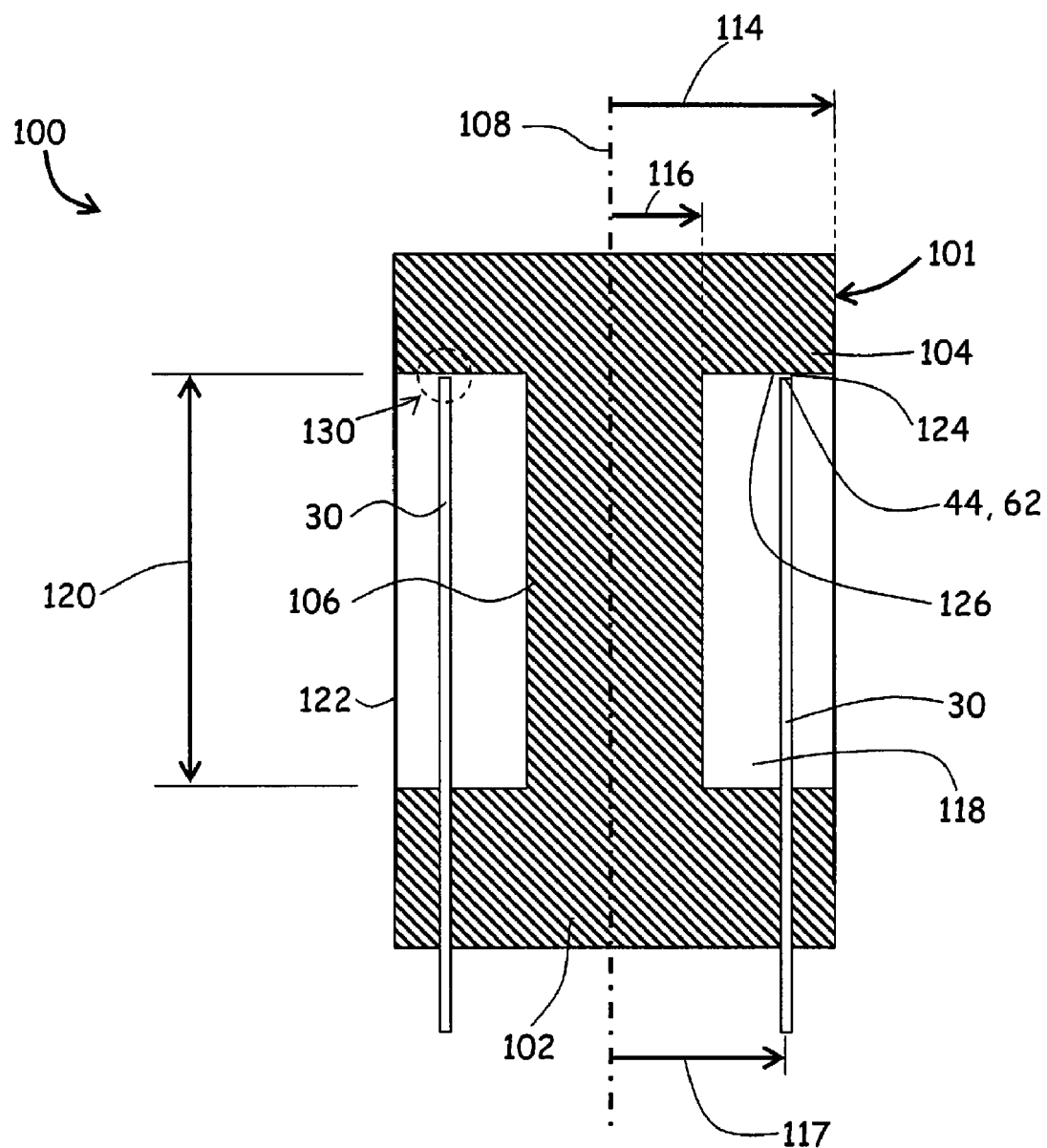
FIG. 10 is an enlarged sectional view of a strain sensor assembly having a unibody structure in an embodiment of the invention.
Figure 11:
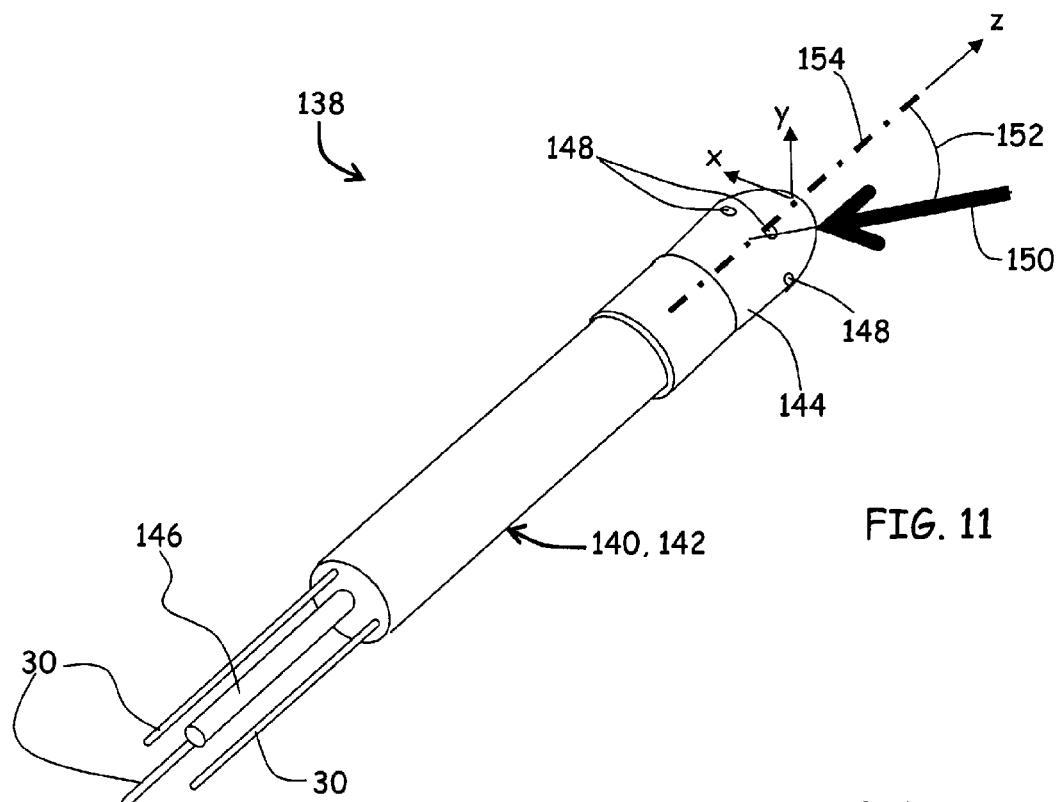
FIG. 11 is a perspective view of an ablation head assembly in an embodiment of the invention.

Referring to FIG. 10, a strain sensor assembly 100 is depicted that includes a unibody structure 101 in an embodiment of the invention. In the depicted configuration, the unibody structure 101 includes a base portion 102 and a distal portion 104 separated by a stem portion 106, all concentric about a central axis 108. The base and distal portions 102 and 104 may be characterized by a major radius 114 and the stem portion 106 by a minor radius 116 to define an annular gap 118 having a length 120. The transmitting elements 30 may be located on a sensing radius 117 and extend through the base portion 102 and across a majority of the length 120 to define a gap 124 between the free end 44 of the transmitting element 30 and an inward-facing surface 126 of the distal portion 104. The annular gap 118 surrounded a thin tubular membrane 122 to form a closure 123.

As in the other embodiments disclosed above, the free end 44 of the transmitting element 30 may be configured as a semi-reflecting surface 62. The inward surface 126, or at least the portions immediately opposite free ends 44 of the transmitting elements 30, may be made highly reflective to affect a Fabry-Perot resonator 130 across the gaps 124. The fabrication of the Fabry-Perot resonator 130 in this way eliminates the need for reflecting elements 32.

The tubular membrane 122 may be of similar construction as discussed in connection with strain sensor assembly 94 to retain the same advantages. The unibody structure 101 may be made from a material having a CTE similar to that of the transmitting elements 30. Matching the CTEs of the structural element 101 and the transmitting elements 30 may be accomplished by fabricating the unibody structure 101 from the same material as the transmitting elements 30. However, materials suitable for fiber optic applications tend to be quite stiff, as measured by the modulus of elasticity or the so-called "Young's modulus." Quartz, for example, has a Young's modulus of approximately 70 GPa. Compare this with, for example, structural polymers having a Young's modulus typically of 1 to 10 GPa. The result is that the unibody structure 101 as depicted that is fabricated from quartz is relatively stiff and will have a reduced sensitivity to applied forces relative in comparison with the strain sensor assemblies 20, 90 and 94.

Alternatively, the unibody structure 101 may be comprised of a material that closely matches the CTE of the transmitting elements 30 but possesses less stiffness. One such material is liquid crystal polymer (LCP). The material properties of certain LCPs may be found in "DUPONT ZENITE LCP liquid crystal polymer resin," publication K-15415, May 2006, which is hereby incorporated by reference herein other than any express definitions of terms specifically defined therein. LCPs may be fabricated for a CTE that is $5.0\text{-}\times 10^{-6}$ per Kelvin ($5.0\text{-}\mu/K$) or less. A range of approximately 0.5- to $2.0\text{-}\mu/K$ is comparable with quartz. The Young's modulus, however, is on the order of 15 GPa, several factors lower than quartz.

The extent to which the CTEs are matched may be dictated by the particular application. One application or design may not require the same degree of accuracy in the determination of strain as another, or may not require operation over a broad range of temperatures. For example, CTEs of the various components may require closer matching if the strain sensor 20 is to operate over an operating range of 40° C. than an operating range of 5° C. Also, one configuration may have a higher mechanical amplification or gain than another which may allow for more tolerance in the matching of the various CTEs. The artisan may use expressions such as detailed in Eqns. (1) through (6) above to establish a tolerable difference between the various CTEs and still provide a relatively consistent indication of contact force result over a range of temperatures.

In operation, the unibody structure 101 will generally deform or deflect more readily under a force load for the lower Young's modulus while maintaining a suitable insensitivity to bulk temperature changes because of the closely matched CTEs of the materials, as described above. An added benefit of utilizing the unibody structure 101 in the strain sensor assembly 100 is the elimination of glued or bonded joints that are load bearing. Bonding joints may tend to undergo plastic deformation and/or molecular slippage at bonding interfaces when subjected to even moderate loads. Bonding materials having a substantially different CTE may also contribute to thermal expansion errors of the assembly. These characteristics may be manifested as a hysteresis or a bias error in the strain measurement. The unibody structure 101 is free of bonded joints that experience a force load in operation. It is noted that the transmitting elements 30 may be bonded to the base portion 102, but these bonds do not support a structural load due to application of a force vector on the distal portion 104.

The sensitivity of the strain sensor assembly 100 may be further controlled by the sizing of the major and stem radii 114, 116. The deflection at the locations of the gaps 124 under a given force applied to the distal portion 104 will generally increase as the stem radius 116 is decreased. The angular deflection (i.e. rotation about an axis that is orthogonal to the central axis 108) of the distal portion due to an eccentric force component will tend to be amplified as the ratio of the sensing radius 117 to the stem radius 116 is increased.

Referring to FIGS. 11 through 17, an end effector 142 that includes a strain sensor assembly 140 within an ablation head assembly 138 is portrayed in an embodiment of the invention. The particular end effector 142 portrayed includes a radiofrequency (RF) ablator head 144. Various appurtenances may be utilized in the operation of the end effector 142. In the case of the RF ablator head 144, such appurtenances may include an irrigation tube 146 in fluid communication with the RF ablator head 144 that effuses coolant through exit passages 148. A plurality of transmitting elements 30 extend into the strain sensor assembly 140.

While the following discussions are directed to the ablation head assembly 138, it is understood that a variety of end effectors may be utilized and still be within the scope of the invention. Depending upon the specific treatment to be applied to the vessel or organ, the catheter may comprise any of a number of end effectors, such as but not limited to RF ablation electrodes, rotary or scissor action cutting heads, laser ablation system, injection or sewing needles, fluid conveyance systems, forceps, manipulators, mapping electrodes, endoscopic vision systems and therapeutic delivery systems such as genetic impregnation devices.

A force vector 150 is depicted as being applied to the RF ablator head 144, the force vector 150 being characterized by an orientation that presents an angle of application 152 between the force vector 150 and a central axis 154 of the ablation head assembly 138. In practice, the force vector 150 may be in reaction to the end effector 142 being brought into contact with an object such as the interior wall of a vessel or organ. The central axis may define the z-axis of an x-y-z coordinate system with origin at the distal extremity tip of the RF ablator head 144.

Figure 12:
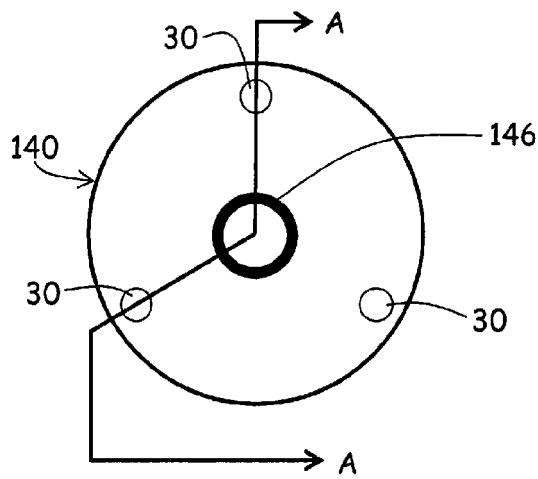
FIG. 12 is an end view of the ablation head assembly of FIG. 11.
Figure 13:
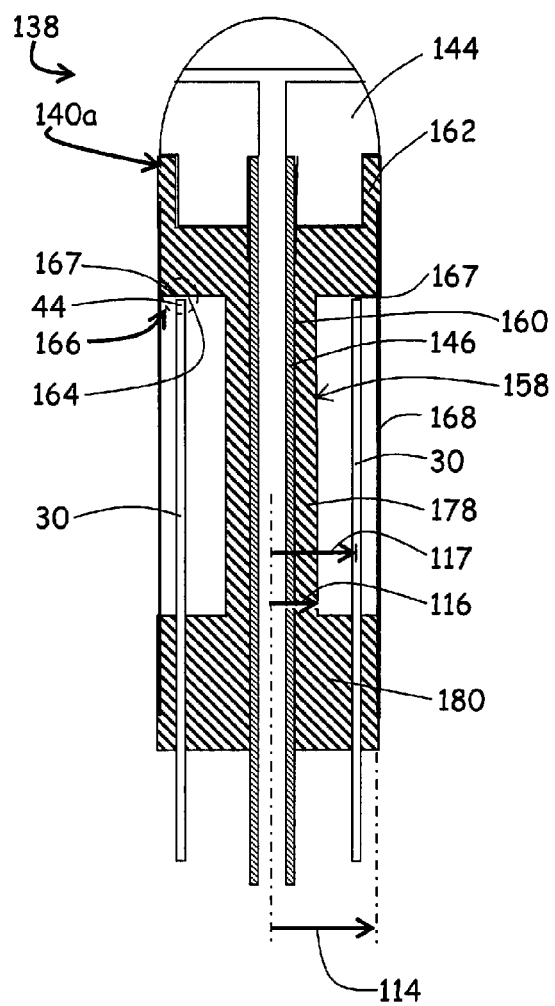
FIG. 13 is an enlarged sectional view of a first embodiment of the ablation head assembly of FIG. 11.

The cross-section A-A of FIG. 12 is depicted in FIGS. 13 through 17 for various embodiments of the invention. FIG. 13 illustrates the ablation head assembly 138 as having a strain sensor assembly 140a that includes a unibody structure 158 having a center bore 160 that accommodates the irrigation tube 146. A distal portion 162 of the unibody structure 158 includes a reflective surface 164 that cooperates with the free ends 44 of the transmitting element 30 to create a Fabry-Perot resonator 166 across a gap 167. The unibody structure 158 is wrapped with a thin membrane 168 to maintain keep the gaps 167 free of bodily fluids during operation.

The unibody structure 158 made of a material such as LCP to match the CTE of the transmitting elements 30. The irrigation tube 146 may also be made of a material that closely matches the CTE of the unibody structure 158, such as the same material as the unibody structure 158 or the same material as the transmitting elements 30.

Figure 14:
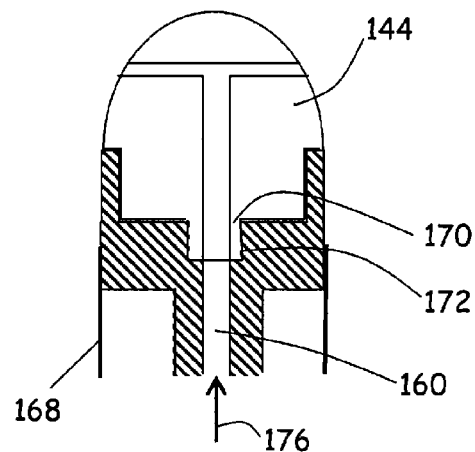
FIG. 14 is an enlarged partial sectional view of a head configuration in an embodiment of the invention.
Figure 15:
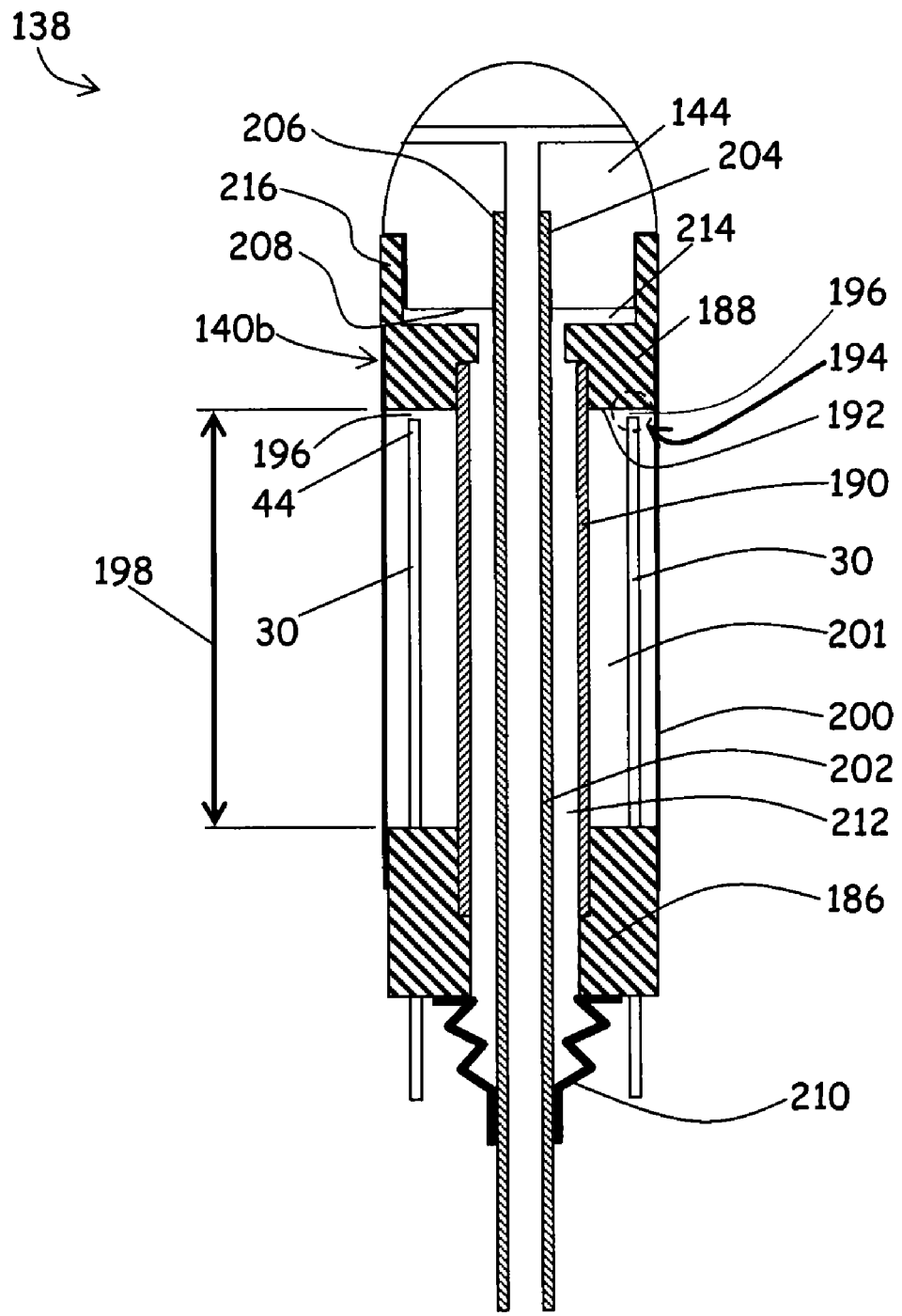
FIG. 15 is an enlarged sectional view of a second embodiment of the ablation head assembly of FIG. 11.

An alternative arrangement for the RF ablator head 144 and the distal portion 162 of the unibody structure 158 is portrayed in FIG. 14. The RF ablator head 144 includes an extension portion 170 for the irrigation passage. The extension portion 170 cooperates with a socket or recess 172 on the distal portion 162 to create a joint that provides flow continuity between the center bore 160 and the RF ablator head 144.

In operation, a coolant 176 is routed through the irrigation tube 146. The coolant 176 may have to run substantially cooler than the ambient working environment of the catheter in order adequately cool the RF ablator head 144. A contraction of the irrigation tube 146 may exert a compressive force on the unibody structure 158 that translates into a reduction in the dimension of the gaps 167, thus casing an error in the apparent strain reading. By selecting a material that closely matches the CTE of the unibody structure 158, the deleterious effects of differential thermal expansion between the irrigation tube 146 and the unibody structure 158 may be substantially reduced.

The alternative arrangement of FIG. 14 also reduces the effects of differential thermal expansion. The center bore 160 carries the coolant directly, thereby eliminating the need for and the potential CTE differential presented by the irrigation tube 146.

The reduction or elimination of dissimilar CTEs in material selection, however, does not necessarily preclude the elimination of thermal expansion effects. For materials that have a non-zero CTE, there can still be thermal distortion due to the presence of thermal gradients within the assembly. Perfectly matched CTEs do not prevent different components or portions of components from expanding or contracting to different dimensions due to differences in temperature.

Consider, for example, the effect of thermal gradients on the ablation head assembly 138 of FIG. 13 or 14. Non-limiting examples of the operating temperatures in a given application are 40 degrees Celsius (° C.) for the RF ablator head 144, 26° C. for the coolant 176 and an ambient medium or working environment temperature of 37° C. The coolant 176 is in close thermal coupling with the irrigation tube 146 and a stem portion 178 of the unibody structure 158, causing the stem portion 178 to operate at a temperature close to that of the coolant 176. In contrast, the RF ablator head 144, when operating at the higher temperature, conducts heat to the distal portion 162 of the unibody structure 158. Hence, in the case of an RF ablation cathode, the temperature extremes of the system are represented at the RF ablator head 144 and the irrigation tube 146. The resulting increased temperature of the distal portion 162 may cause it to expand and deform, particularly out at the sensing radius 117 which thermally is more closely coupled to the RF ablator head 144 than to the stem portion 178.

In addition, the transmitter elements 30 extend from a base portion 180 of the unibody structure at the sensing radius 117, which may be located closer to the major radius 114 than to the stem radius 116 to increase the force sensing resolution of the ablation head assembly 138. In this case, the base portion 180 at the location of the sensing radius 117 will be more closely thermally coupled to the ambient medium in which the ablation head assembly 138 is immersed. This introduces a third temperature that further contributes to thermal gradients. The transmitting elements 30 are conductively coupled to this third temperature, and may experience a thermal expansion relative to the stem portion 178.

The combination of the cooler temperature of the stem portion 178, the warmer temperature of the distal portion 162 and the intermittent temperature of the base portion 180 may cause a change in the dimension of the gap 167 that translates to an apparent and false change in the strain. These effects are inherent to any assembly that has components with a non-zero CTE.

Thermal gradients can be militated against by isolating the structural components that establish the dimension of the gap 167 from temperature extremes. An embodiment that utilizes this principle is presented in FIG. 15. The ablation head assembly 138 depicted therein utilizes a strain sensor assembly 140b that includes a proximal portion 186 and distal portion 188 separated by a single tube standoff member 190, with the free ends 44 of the transmitting elements 30 and an opposing face 192 of the distal portion 188 affecting a Fabry-Perot resonator 194 having a gap 196. The strain sensor assembly 140b combines the single support tube concept of FIG. 6 with the reduced stem radius and the reflective face on the distal portion concepts of FIG. 10. An active length 198 is defined by the distance between opposing faces of the proximal and distal portions 186 and 188, and is shrouded from the ambient medium with a tubular membrane 200. An insulative annular gap 201 is formed between the tubular membrane 200 and the single tube standoff member 190.

An irrigation tube 202 may be aligned in substantial concentricity with the single tube standoff member 190. The irrigation tube 190 is supported at a distal end 204 within a socket 206 formed on a bottom face 208 of the RF ablator head 144. The irrigation tube 190 is held in substantial concentric alignment with the single tube standoff member 190 by a bellows member 210 that depends from the proximal portion 186. A radial insulative gap 212 is thereby defined in the form of an annulus between the exterior diameter of the irrigation tube 202 and the interior diameter of the single tube standoff member 190. An axial insulative gap 214 may also be provided between the bottom face 208 of the RF ablator head 144 and the distal portion 188 of the strain sensor assembly 140b.

The single tube standoff member 190 may be fabricated from a variety of materials, as disclosed in the discussion attendant FIG. 6. The bellows 210 may be of a complaint material that offers little resistance to axial compression or extension. The various insulative gaps 201, 212 and 214 may contain any of a number of gases, including air or nitrogen, or gases known for their thermal resistance characteristics such as argon.

In operation, the radial gap 212 thermally isolates the irrigation tube 202 from the strain sensor assembly 140b. In practical terms, thermal coupling between the irrigation tube 202 and strain sensor assembly 140b is limited to conduction through the bellows member 210 and conduction and convection through the gas that fills the radial gap 212. Heat transfer via conduction between the irrigation tube 202 and the RF ablator head 144 contributes to the cooling of the RF ablator head 144 and essentially does not cool the strain sensor assembly 140b. The axial gap 214 serves to thermally isolate the RF ablator head 144 from the distal portion 188, so that the conduction path is limited to a collar portion 216 that is formed on the distal portion 186.

Accordingly, the components that define the gap dimension (i.e. the distal and proximal portions 186 and 188, the single tube standoff member 190 and the transmitting elements 30) are substantially thermally isolated from the extreme temperatures posed by the coolant 176 and the Joule-heated RF ablator head 144.

Figure 16:
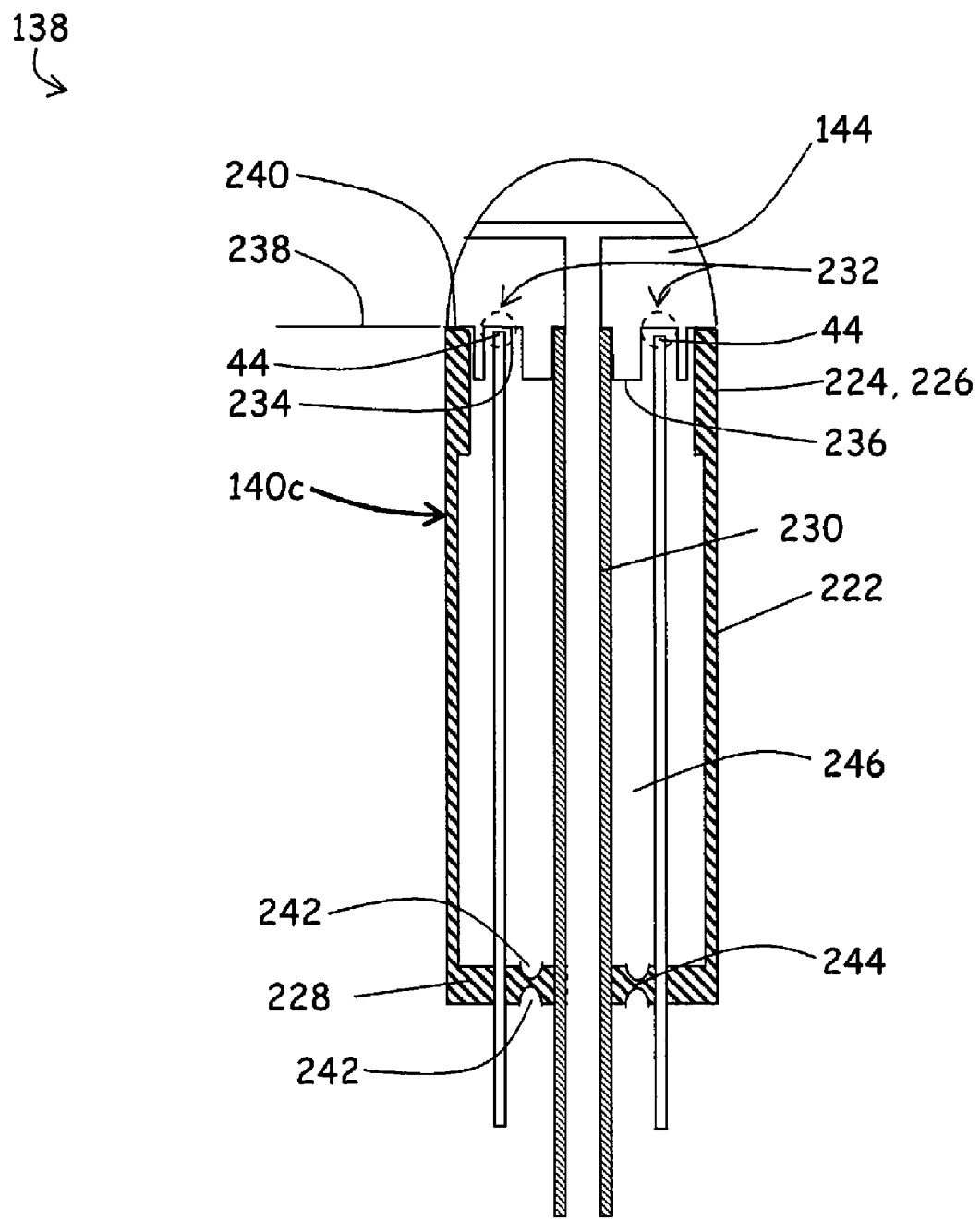
FIG. 16 is an enlarged sectional view of a third embodiment of the ablation head assembly of FIG. 11.

Another embodiment that incorporates the principles of thermal isolation for reduction of thermal gradients, and also utilizes an end effector in the formation of an interferometric gap, is presented in FIG. 16. The ablation head assembly 138 includes a strain sensor assembly 140c that includes a unibody structure 222 having a collar portion 224 at a distal end 226 and a base portion 228, the unibody structure 222 being in coaxial alignment with an irrigation tube 230. The transmitting members 30 form a plurality of Fabry Perot resonators 232 between the free ends 44 and a recessed reflective face 234 of the RF ablator head 144. The recessed reflective face 234 is axially offset with respect to a bottom face 236 of the RF ablator head 144 so that the recessed reflective face is at a datum 238 that is in common with a distal extremity 240 of the collar portion 224. The base portion 228 may include annular grooves 242 that define a flexure 244. The coaxial arrangement between the strain sensor assembly 140c and the irrigation tube 230 defines an annular gap 246.

Functionally, the location of the recessed reflective face 234 on the same datum 238 as the distal extremity 240 of the strain sensor assembly 140c substantially precludes movement of the recessed reflective face 234 relative to the distal extremity 240. For example, thermal expansion of the RF ablator head 144 causes it to grow outward from the datum 238, but does not change the position of the recessed reflective face 234 relative to the datum 238. Hence, the dimension of the Fabry Perot resonator is not affected by the differential thermal expansion between of the RF ablator head 144 and the unibody structure 222.

The flexure 244 provides compliance that accommodates thermal expansion or contraction of the irrigation tube 230 that reduces the strain translated to the body of the unibody structure 222. The flexure 244 also reduces the conductive coupling between the irrigation tube 230 and the base portion 228. The annular gap 246 provides thermal isolation between the irrigation tube 230 and the unibody structure 222, as well as between the irrigation tube 230 and the transmitting elements 30. The unibody structure 222 also encapsulates the transmitting elements 30, eliminating the need for a tubular membrane.

Figure 17:
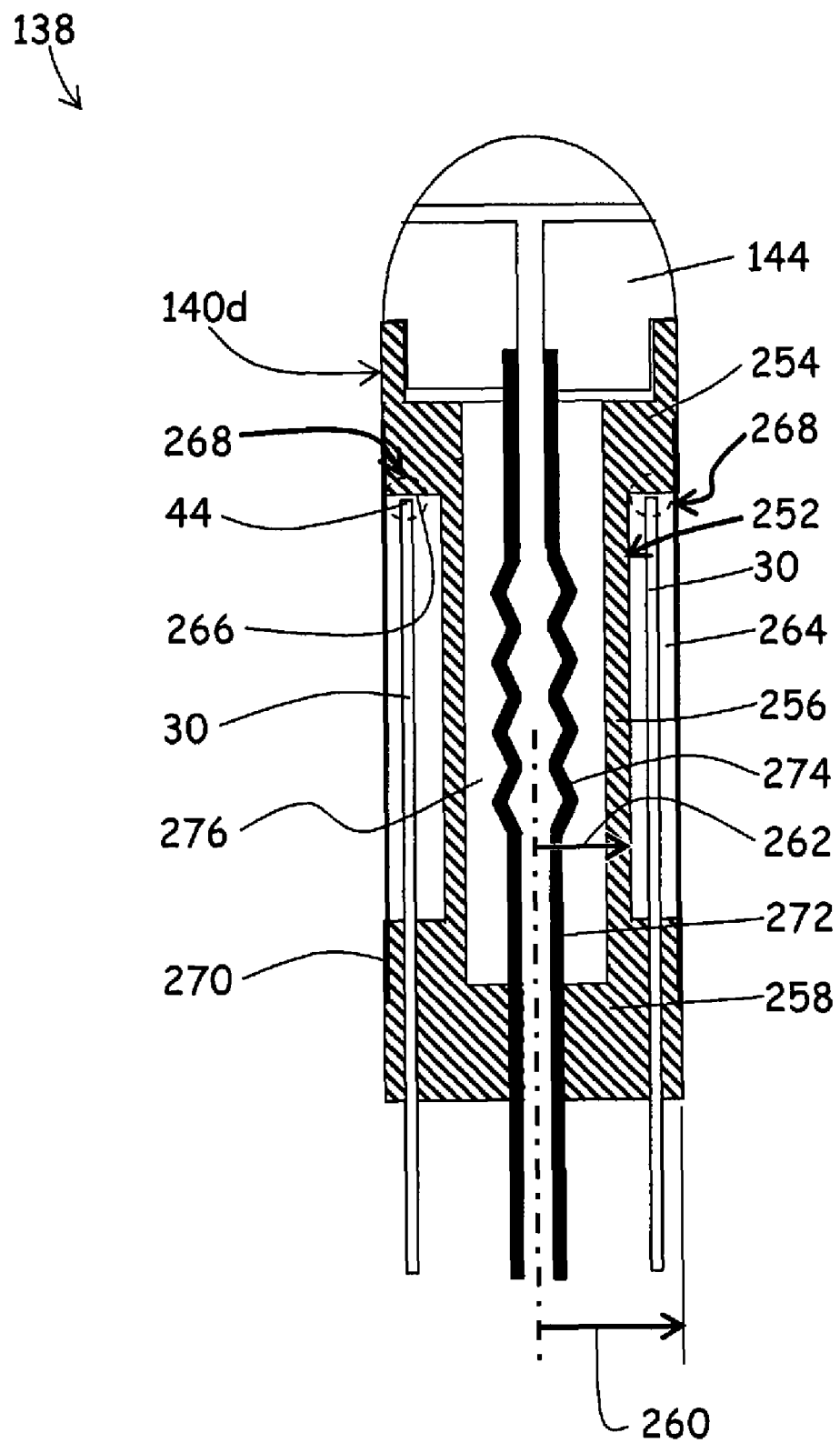
FIG. 17 is an enlarged sectional view of a fourth embodiment of the ablation head assembly of FIG. 11.

FIG. 17 depicts another embodiment of the present invention. The ablation head assembly 138 comprises a strain sensor assembly 140d having a unibody structure 252 with a distal portion 254, a stem portion 256 and a base portion 258. In this embodiment, the base and distal portions 258 and 254 are characterized by a major radius 260, and the stem portion by a stem radius 262 that is less than the major radius 260. The difference in radii 260 and 262 creates an annular gap 264. The transmitting elements 230 extend into the annular gap 264, with the free ends 44 and a reflective bottom surface 266 of the distal portion 254 to create a plurality of Fabry-Perot resonators 268. A tubular membrane 270 encapsulates the annular gap 264.

An irrigation tube 272 is concentric with the strain sensor assembly 140d. The irrigation tube 272 includes a bellows portion 274 that extends at least partially between the RF ablator head 144 and the base portion 258 of the unibody structure 252. A radial gap 276 is defined between the bellows portion 274 and the stem portion 256 of the strain sensor assembly 140d.

A distinction of the strain sensor assembly 140d embodiment is the bellows portion 274 of the irrigation tube 272. The bellows portion 274 may be designed for substantial radial stiffness through the use of radially-oriented fibers or cords, while remaining compliant in the axial direction.

In operation, the axial compliance mitigates against inducement of strain in the unibody structure 252 as the bellows portion 274 expands and contracts. Otherwise, the function of the various gaps depicted in FIG. 17 provide thermal isolation between the irrigation tube 272, RF ablator head 144 and the unibody structure 252. The tubular membrane 270 provides relief due to thermal expansion and contraction of the gas entrapped in the annular gap 264, as discussed in connection with FIG. 8.

Figures 18, 19:
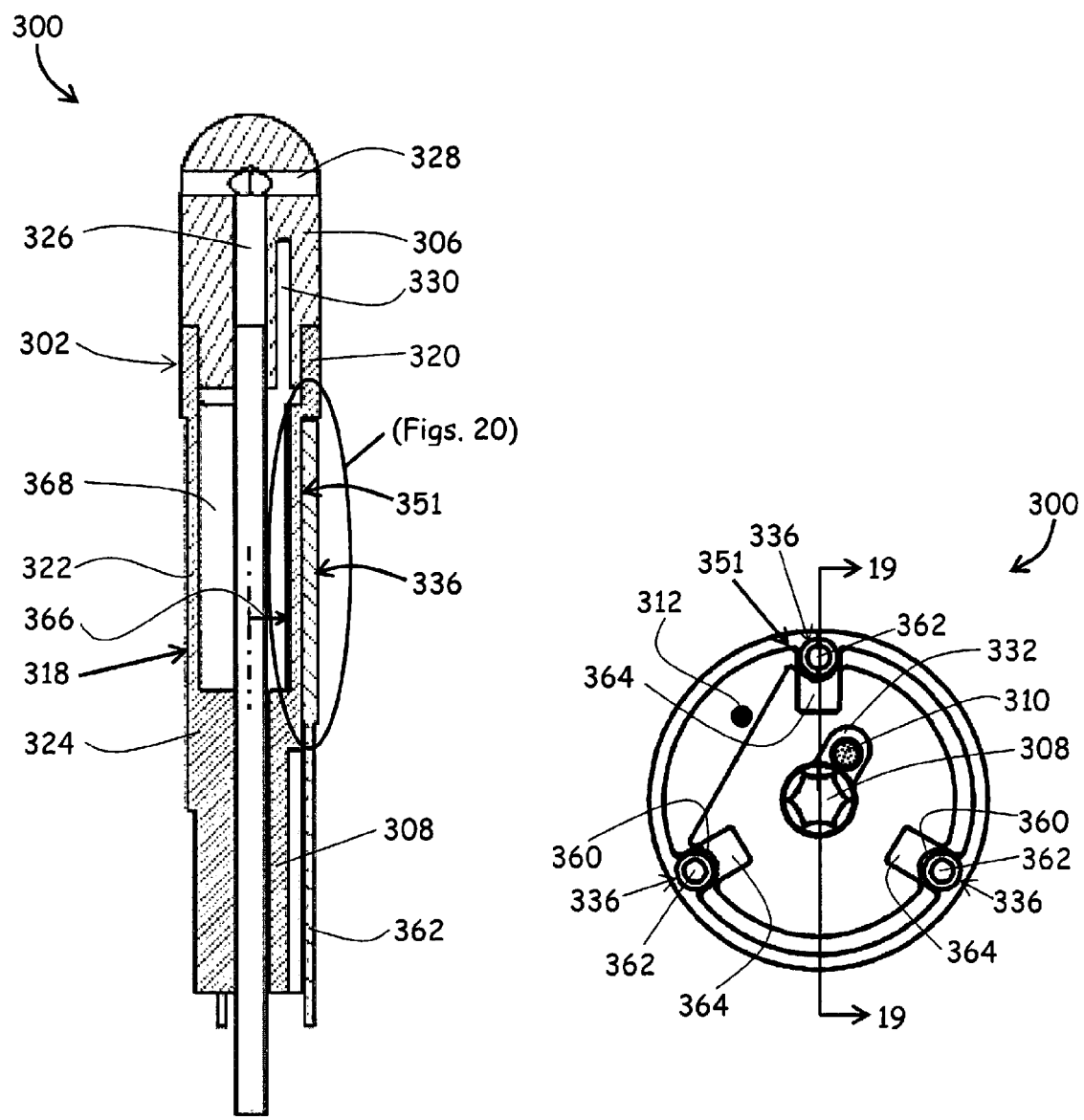
FIG. 18 is an enlarged end view of an ablation head assembly in an embodiment of the invention.
FIG. 19 is a cross-sectional view of the ablation head assembly of FIG. 18.

Referring to FIGS. 18 through 20, an embodiment of a ablation head assembly 300 including a strain sensor assembly 302 and a radio-frequency (RF) ablator head 306. The ablation head assembly 300 may include numerous appurtenances for effective operation, including but not limited to an irrigation tube 308, an RF cable 310 and a temperature sensor 312 for monitoring the temperature of the RF ablator head 306.

In this embodiment, the strain sensor assembly 302 includes a unibody structure 318 having a collar portion 320, a stem portion 322 and a base portion 324. The RF ablator head 306 is secured within the collar portion 320, and includes a central bore 326 in fluid communication with exit passages 328 that may provide for cooling of the RF ablator head 306 both internally and by film cooling of the exterior. A thermocouple port 330 may be formed in the RF ablator head 306. The RF cable 310 may be routed through an access port 332 adjacent the irrigation tube 308.

The strain sensor assembly 302 may utilize a plurality of strain sensors 336 that may be of a coaxial construction and may include a transmitting element 338 and a reflecting element 340, each attached to an outer tubular portion 342 at contact locations 344 and 346. A Fabry-Perot resonator 347 having an operative length 349 is defined between the free ends of the transmitting and reflecting elements 338 and 340. The strain sensors 336 may be further characterized by a proximal end 348 and a distal end 350.

Figure 20A:
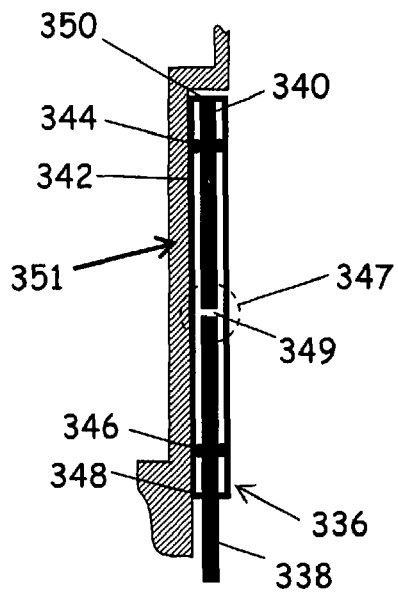
FIGS. 20A through 20D are expanded views of mounting arrangements of the strain sensor of FIG. 19.

Referring to FIG. 20A, the strain sensors 336 may be bonded directly to the unibody structure 318 across a continuous length of the strain sensor 336. One bonding technique may involve the use of a solvent designed to cause the material of the unibody structure 318 to melt or flow while not affecting the material of the strain sensor 336. The solvent may be applied to an area or zone 351 of the unibody structure 318 where the strain sensors 336 are to be mounted, and the strain sensor 336 placed thereon. Alternatively, the strain sensors 336 may be temporarily held in place on the zone 351 of the unibody structure 318 and the solvent applied to both. The flowing of the material in the zone 351 causes a bond between the unibody structure 318 and the outer tubular portion 342 of the strain sensor 336. The solvent may be removed by a process such as washing or evaporation to arrest the melting process. The use of the solvent may also be incorporated with separate or non-unibody structures, such as depicted in FIG. 1 through 9, to mount standoff members 28 or 190.

Figure 20B:
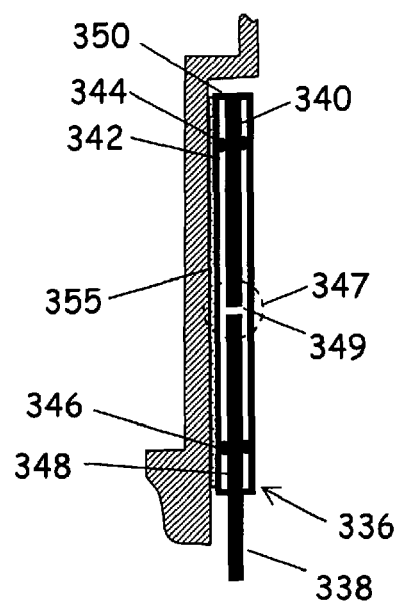

Referring to FIG. 20B, an embodiment of the invention wherein the strain sensors 336 are bonded to the unibody structure 318 using a bonding agent 355 such as glue or epoxy is depicted. The bonding agent 355 may be selected for closest available CTE, or for flexibility so that the thermal growth of the adhesive film does not impose a substantial strain on the strain sensor 336. Use of a very thin film of bonding agent 355 may also mitigate the effects of differential thermal expansion.

Figure 20C:
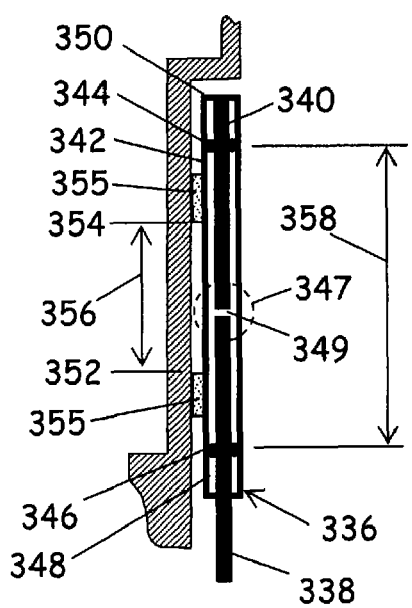
Figure 20D:
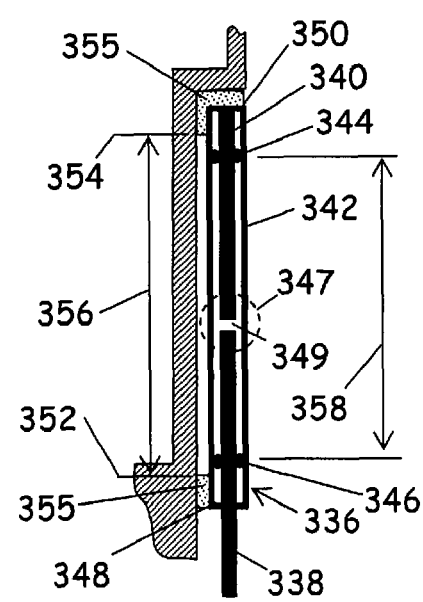

Referring to FIGS. 20C and 20D, an embodiment of the invention is depicted wherein each strain sensor 336 may be mounted to the unibody structure 318 at two locations: a proximal location 352 near the proximal end 348 and a distal location 354 near the distal end 350. The bonding agent 355 is discontinuous along a span distance 356. An active length of the strain sensor 336 may be defined by a span distance 356 between the proximal and distal locations 352 and 354, or by a separation distance 358 between contact locations 344 and 346, whichever is less. Accordingly, the active length for the configuration of FIG. 20C is generally the span distance 356, whereas the active length of the configuration of FIG. 20D is generally the separation distance 358.

Because the contact length between the strain sensing element 336 and the bonding agent 355 is limited, the CTE of the bonding agent 355 may be substantially dissimilar without introducing unacceptable error to the strain measurement.

The unibody structure 318 may be formed with grooves 360 that enable the strain sensing elements 336 to be mounted thereto without increasing the radial profile of the ablation head assembly 300. Each strain sensing element 336 has a fiber optic lead cable 362 that is in communication with the strain sensing elements 336. The fiber optic lead cables 362 may be routed through slots 364 formed in the base portion 324. The stem portion 322 has an inner diameter 366 that is larger than the outer diameter of the irrigation tube 308, thus providing an annulus 368. The irrigation tube 308 is fabricated from a thin-walled, compliant tubing material that imposes a small or negligible strain on the unibody structure 318 when undergoing expansion or contraction.

Representative and non-limiting dimensions for the ablation head assembly 300 include an overall length of approximately 15- to 20-mm, an outer diameter of 2.3- to 2.6-mm (7 to 8 French) and a length of the strain sensor 336 of approximately 5- to 10-mm. The irrigation tube 308 may be a thin, tubular membrane having a wall thickness on the order of 10- to 20-micrometers (μm). When implemented, an exemplary and non-limiting dimension for the clearance between the irrigation tube 308 and the inner diameter 366 of the stem portion 322 is 200- to 300-μm. Exemplary operative lengths 349 may range from 10- to 50-μm.

In operation, strain that is experienced by the unibody structure 318 is translated to the outer tubing portion 342 of the strain sensor 336 via the bonding agents 355 at the proximal and distal locations 352 and 354. The strain experienced by the outer tubing portion 342 causes the transmitting and reflecting elements 338 and 340 to translate along the central axis of the strain sensor 336, thereby altering the dimension of the Fabry-Perot resonator 347. The magnitude of the translation is the same as the magnitude of the relative movement between contact locations 344 and 346. For configurations where the distance 358 between contact locations 344 and 346 is less than the span distance 356 between the proximal and distal locations 352 and 354, such as depicted in FIG. 20C, only the translation between contact locations 344 and 346 is sensed by the Fabry-Perot resonator. However, for configurations where the span distance 356 is less than the distance 358, such as depicted in FIG. 20D, only the translation between the proximal and distal locations 352 and 354 may be sensed because the portions of the outer tube 342 located outside the span distance 356 are not strained.

The annulus 368 separates the irrigation tube 308 from the stem portion 322, providing some of the thermal isolation advantages and effects previously discussed.

A method of inferring a three-dimensional force vector (magnitude and direction) from strain and temperature measurements to a force vector having magnitude is presented in International Publication No. WO 2007/015139 to Leo, et al., the disclosure of which is hereby incorporated by reference other than any express definitions of terms specifically defined therein. A modification to the method sans temperature measurements is presented below.

An elastic strain ε corresponding to a given change in the operative length of an interferometric gap may be determined with commercially available instruments, such as the FTI-10 Single-Channel Signal Conditioner marketed by FISO Technologies, Inc. of Quebec, Canada. Consider the strain sensor assembly of FIG. 18, depicting the three strain sensors 336. The elastic strains ε are related to the internal forces experienced by the standoff member(s) as a function of the physical dimensions and the material properties of the deformable body.

$$\begin{bmatrix} \varepsilon_{el1,t} \\ \varepsilon_{el2,t} \\ \varepsilon_{el3,t} \end{bmatrix} = \begin{bmatrix} 1 & y_1 & -x_1 \\ 1 & y_2 & -x_2 \\ 1 & y_3 & -x_3 \end{bmatrix} \cdot \begin{bmatrix} \frac{1}{E_{ten} \cdot A} & 0 & 0 \\ 0 & \frac{1}{E_{flex} \cdot I_x} & 0 \\ 0 & 0 & \frac{1}{E_{flex} \cdot I_y} \end{bmatrix} \cdot \begin{bmatrix} N_{z,t} \\ M_{x,t} \\ M_{y,t} \end{bmatrix} \quad \text{Eqn. (7)}$$

$$\varepsilon_{el,t} = G \cdot \delta \cdot I_{F,t}$$

Where:
 $x_i$ and $y_i$, i=1, 3—coordinates of gap interferometer with respect to center of gravity of the catheter cross-section $\varepsilon_{elij}$, i=1, 3—elastic strain values at time t $E_{ten}$—Equivalent tension/compression Young modulus of catheter $E_{flex}$—Equivalent flexural Young modulus of catheter $I_x$—Moment of inertia with respect to x axis $I_y$—Moment of inertia with respect to y axis $N_{z,t}$—Normal force in direction of z axis at time t $M_{x,t}$—Bending moment with respect to x axis at time t $M_{y,t}$—Bending moment with respect to y axis at time t G—Geometry matrix δ—Matrix of flexibility $I_{F,t}$—Matrix (vector) of internal forces at time t Equation (7) may be rearranged to solve for the internal forces as a function of the elastic strain:

$$\begin{bmatrix} N_{z,t} \\ M_{x,t} \\ M_{y,t} \end{bmatrix} = \begin{bmatrix} E_{ten} \cdot A & 0 & 0 \\ 0 & E_{flex} \cdot I_x & 0 \\ 0 & 0 & E_{flex} \cdot I_y \end{bmatrix} \cdot \begin{bmatrix} 1 & y_1 & -x_1 \\ 1 & y_2 & -x_2 \\ 1 & y_3 & -x_3 \end{bmatrix}^{-1} \cdot \begin{bmatrix} \varepsilon_{el1,t} \\ \varepsilon_{el2,t} \\ \varepsilon_{el3,t} \end{bmatrix} \quad \text{Eqn. (8)}$$

$$I_{F,t} = S \cdot G^{-1} \cdot \varepsilon_{el,t}$$

Where: $S = \delta^{-1}$—Stiffness matrix

The internal forces experienced by the optical fiber sensors are computed based on the positions of the optical fiber sensors from the exterior wall of the deformable body, assuming the deformable body is substantially incompressible:

$$\begin{bmatrix} F_{x,t} \\ F_{y,t} \\ F_{z,t} \end{bmatrix} = \begin{bmatrix} 0 & 0 & -\frac{1}{d} \\ 0 & \frac{1}{d} & 0 \\ -1 & 0 & 0 \end{bmatrix} \cdot \begin{bmatrix} N_{z,1} \\ M_{x,t} \\ M_{y,t} \end{bmatrix} \quad \text{Eqn. (9)}$$

$$F_t = d \cdot I_{F,t}$$

Where:

$F_{x,t}$—Touching external transversal force at time t, in direction of x axis (with opposite sense)

$F_{y,t}$—Touching external transversal force at time t, in direction of y axis (with opposite sense)

$F_{z,t}$—Touching external normal force at time t in direction of z axis (with opposite sense, compression is positive)

d—distance between the touching point of lateral forces and the cross-section with sensors (along z axis)

$F_t$—Matrix of touching external forces at time t d—Matrix of conversion

The solution of Eqns. (7) through (9) provides a normal and a transverse force applied to the external surface of the deformable body, i.e., $F_{norm,t} = F_{z,t}$ and $F_{trans,t}$=square root $(F^2_{x,t} + F^2_{y,t})$ An angle of application $\gamma_t$ of the transverse force may be computed from Table I:

TABLE I

| $F_{x,t}$ | $F_{y,t}$ | $\gamma_t$ |
|---|---|---|
| $\geq 0$ | $\geq 0$ | $\arcsin(F_{y,t}/F_{tran,t})$ |
| $<0$ | $\geq 0$ | $\Pi - \arcsin(F_{y,t}/F_{tran,t})$ |
| $<0$ | $<0$ | $\Pi + \arcsin(F_{y,t}/F_{tran,t})$ |
| $\geq 0$ | $<0$ | $2 * \Pi - \arcsin(F_{y,t}/F_{tran,t})$ |

Equations (7) through (9) are related to the material properties of the deformable body or optical fiber sensors, such as the elastic moduli of the deformable body. Other values, such as the coordinate distances between the optical fiber sensors, the operative lengths of the interferometric gaps and the external surface of the deformable body may be subject to variations as a consequence manufacturing tolerances.

To improve the accuracy of the computed force vector, specific information for each deformable body may be stored in storage device 79. Generally, the information make take the form of a data file that is input to console 77 prior to use of the strain sensor assembly 20. For example, storage device 79 may comprise a memory chip associated with the transmitting/receiving line 84 in which such information is stored, or a bar code or a RFID tag located on the body of the strain sensor assembly 20 or on the packaging. Alternatively, data specific to an individual deformable body may be uploaded to console 77 from an item of removable storage (e.g., CD) or via secure download from the manufacturer's website.

The information specific to each deformable body may be obtained during a calibration step, conducted during manufacture of the deformable body, by subjecting the deformable body to a series of known forces. In this case, the foregoing equations may be collapsed so the normal and transverse forces may be computed directly from a strain-to-force conversion matrix:

$$F(t) = K(\epsilon(t) - \epsilon_0) \qquad \text{Eqn. (11)}$$

where F(t) is the vector of forces $[F_{x,t}, F_{y,t}, F_{z,t}]$ (corresponding for example to the force vector 150 of FIG. 11), $\epsilon(t)$ is the vector of strains $[\epsilon_{1,t}, \epsilon_{2,t}, \epsilon_{3,t}]$ of the interference pattern measured for the individual sensors, $\epsilon_0$ is the vector of strains $[\epsilon^0_1, \epsilon^0_2, \epsilon^0_3]$ measured for the individual sensors with zero applied force, and K is a matrix computed when the deformable body is subjected to the series of known forces During the calibration step of manufacture, in constant temperature conditions, the deformable body is subjected to the following forces in series: (1) a purely axial force of known magnitude $F_{z,t}$; (2) a lateral force of known magnitude $F_{x,t}$; and (3) a lateral force of known magnitude $F_{y,t}$ applied 90 degrees to the orientation of force $F_{x,t}$. When all of the forces $[F_{x,t}, F_{y,t}, F_{z,t}]$ and wavelengths are known, the force-to-strain conversion matrix K may be computed as:

$$K = F(\epsilon(t) - \epsilon_0)^{-1} \qquad \text{Eqn. (12)}$$

or:

$$\begin{bmatrix} F_x & 0 & 0 \\ 0 & F_y & 0 \\ 0 & 0 & F_z \end{bmatrix} \begin{bmatrix} (\epsilon_1 - \epsilon^0_1) & (\epsilon'_1 - \epsilon^0_1) & (\epsilon''_1 - \epsilon^0_1) \\ (\epsilon_2 - \epsilon^0_2) & (\epsilon'_2 - \epsilon^0_2) & (\epsilon''_2 - \epsilon^0_2) \\ (\epsilon_3 - \epsilon^0_3) & (\epsilon'_3 - \epsilon^0_3) & (\epsilon''_3 - \epsilon^0_3) \end{bmatrix}^{-1} = \begin{bmatrix} k_{11} k_{12} k_{13} \\ k_{21} k_{22} k_{23} \\ k_{31} k_{32} k_{33} \end{bmatrix} \qquad \text{Eqn. (13)}$$

Force-to-strain conversion matrix K then may be stored in storage device 79 associated with the corresponding deformable body, as disclosed herein. The values of the force-to-conversion matrix then may be input to console 77 when the deformable body is coupled to the console using a bar code reader, input pad or direct electrical connection through transmitting/receiving line 84. Once matrix K is provided for a given deformable body, the normal force, transverse force and angle of application of the transverse force may be computed as described above and using Table I.

The values for the normal force, transverse force and angle of application of the transverse force, computed as described above, may be output as numerical values to a display monitor that forms part of console 77. In addition, a graphic including a variable size or colored arrow may be displayed pointing at a position on the circumference of a circle to visualize the magnitude and direction of the transverse force applied to the distal extremity of the deformable body. By monitoring this display, the operator may continuously obtain feedback concerning the contact forces applied to the distal extremity of the deformable body.

The invention may be practiced in other embodiments not disclosed herein, such as endoscopic or additional intravascular applications. For example, various aspects of the disclosed embodiments may be utilized in a diagnostic catheter for optimizing or otherwise improving the placement of excitation electrodes for baroreflex activation. Other aspects of the disclosed embodiments may find application in endoscopic applications, such as orthoscopic surgery or entry through open orifices such as the throat, nose or anus without departing from the spirit of the invention.

References to relative terms such as upper and lower, front and back, left and right, or the like, are intended for convenience of description and are not contemplated to limit the invention, or its components, to any specific orientation. All dimensions depicted in the figures may vary with a potential design and the intended use of a specific embodiment of this invention without departing from the scope thereof.

Each of the additional figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A catheter for use in a medical procedure comprising:
a flexible elongate body defining a central axis and adapted to be introduced into a patient during said medical procedure and including a strain sensing assembly proximate a deformable portion of said elongate body, said strain sensing assembly including:
a proximal portion and a distal portion separated by at least one standoff member to define a separation between said proximal portion and said distal portion,
a plurality of transmitting elements affixed to and extending from said proximal portion of said strain sensing assembly and partially spanning said separation, each of said plurality of transmitting elements including a free end to define a plurality of free ends located between said proximal portion and said distal portion, and
at least one reflecting surface carried by said distal portion of said strain sensing assembly and operatively coupled with at least one of said plurality of free ends to define a plurality of gaps for interferometry, one of said plurality of gaps being presented between each of said plurality of free ends and said at least one reflecting surface, each of said plurality of gaps having an operative length between the respective free end and the at least one reflecting surface, said operative length being variable and responsive to deformation of said deformable portion of said elongate body, said at least one standoff portion and said transmitting element having substantially similar coefficients of thermal expansion in a direction substantially parallel to said operative lengths of said plurality of gaps so that each of said operative lengths remains within a predetermined range when said deformable portion of said elongate body is subject to a predetermined range of bulk temperature change;

one or more sources of electromagnetic radiation operatively coupled to each of said plurality of transmitting elements and transmitting electromagnetic radiation to each of said plurality of gaps to form a plurality of interferometers, each of said interferometers outputting modulated waveforms characteristic of the corresponding of said operative lengths;

one or more receivers operatively coupled to said plurality of transmitting elements to detect said modulated waveforms; and a microprocessor configured to analyze said modulated waveforms to infer a plurality of strains on said deformable portion of said elongate body and to repeatedly resolve a force vector that contacts said catheter distal to said standoff member from said plurality of strains, said force vector including a computed magnitude and an axial component and a transverse component relative to said central axis.

2. The catheter of claim 1 wherein said at least one standoff member includes a plurality of standoff members, said plurality of standoff members equaling the number of said plurality of transmitting elements.

3. The catheter of claim 2 wherein at least one of said plurality of transmitting elements is coaxial with a corresponding one of said plurality of standoff members.

4. The catheter of claim 1 wherein said at least one standoff member is mounted to said proximal portion and said distal portion to define an active length that is at least 100 times greater than each of said operative lengths.

5. The catheter of claim 1 wherein said at least one reflecting surface is disposed on a face of said distal portion.

6. The catheter of claim 1 wherein a difference of said substantially similar coefficients of thermal expansion of said standoff portion and said transmitting element is within 2 μ/K.

7. The catheter of claim 1 wherein said at least one reflecting surface comprises a plurality of reflecting elements, one reflecting element corresponding to each of said plurality of transmitting elements, said plurality of reflecting elements and said plurality of transmitting elements having substantially equal coefficients of thermal expansion.

8. The catheter of claim 1 wherein said interferometer is a Fabry-Perot interferometer.

9. The catheter of claim 1 wherein said at least one standoff member, said proximal portion and said distal portion comprise the same material.

10. The catheter of claim 1 wherein said deformable portion, said tubular outer portion and said transmitting element comprise the same material.

11. The force sensing catheter assembly of claim 1 wherein the coefficient of thermal expansion of said standoff portion is 5 μ/K or less.

12. A device for introduction into a human or animal body comprising:

a flexible elongate body defining a central axis and adapted to traverse a body passageway;

a strain sensor assembly operatively coupled with said flexible elongate body, said strain sensor assembly operatively coupled with an end effector adapted to contact a tissue wall of a vessel or organ, said strain sensor assembly including:

a deformable body operatively coupled with said flexible elongate body and adapted to deform in response to a contact force generated between said end effector and said tissue wall of said vessel or organ, said deformable body including a base portion and a distal portion separated by at least one standoff member, said base portion and said distal portion defining a separation distance therebetween, said deformable body carrying at least one reflecting surface and having a first coefficient of thermal expansion;

a plurality of optical fibers extending from said base portion and partially spanning said separation distance, each of said plurality of optical fibers having a free end that is operatively coupled with said at least one reflecting surface, said plurality of optical fibers having a second coefficient of thermal expansion substantially similar to said first coefficient of thermal expansion, said strain sensor assembly being adapted to provide a repeated indication of a computable force vector corresponding to said contact force, said indication being relatively insensitive to bulk temperature changes over a predetermined operating range of temperatures, said computable force vector including an axial component and a transverse component relative to said central axis.

13. The device of claim 12 wherein said first coefficient of thermal expansion is within 2 μ/K of said second coefficient of thermal expansion.

14. The device of claim 12 further comprising:

one or more sources of electromagnetic radiation operatively coupled to each of said plurality of fiber optic sensors to provide said indication of said contact force;

one or more receivers operatively coupled to said plurality of fiber optic sensors to detect said indication of said contact force;

means operatively coupled to said one or more receivers for analyzing said indication of said contact force to infer at least one component of force on said deformable body.

15. The device of claim 12 wherein first coefficient of thermal expansion of said deformable body is 5 μ/K or less.

16. The device of claim 12 wherein said at least one reflecting surface comprises a plurality of reflecting elements coupled to said deformable body, each one of said plurality of reflecting elements being operatively coupled with a corresponding one of said free end of said plurality of optical fibers.

17. The device of claim 16 wherein said plurality of optical fibers and said plurality of reflecting elements define a plurality of Fabry-Perot resonators.

18. The device of claim 16 wherein each one of said plurality of Fabry-Perot resonators define an operative length that is at least 100 times greater than the dimension of said separation distance.

19. The device of claim 12 wherein said at least one reflecting surface comprises a reflective portion of said deformable body.

20. The device of claim 19 wherein said reflective portion of said deformable body and said plurality of optical fibers define a plurality of Fabry-Perot resonators.

21. The device of claim 19 wherein each one of said plurality of Fabry-Perot resonators define an operative length that is at least 100 times greater than the dimension of said separation distance.

22. The device of claim 12 wherein said end effector comprises a radio frequency ablator head in fluid communication with an irrigation tube, the device further comprising means for thermally isolating said irrigation tube from said deformable structure.

23. The device of claim 12, wherein said at least one standoff member is a stem portion.

24. The device of claim 23, wherein said central axis is coaxial with said base portion and said distal portion of said deformable body, said stem portion having a first radius, said plurality of optical fibers being substantially parallel to and at a second radius from said central axis, said second radius being greater than said first radius.

25. The device of claim 12, wherein said at least one standoff member is a plurality of standoff members.

26. The device of claim 25 wherein each of said plurality of standoff members is coaxial with a corresponding one of said plurality of optical fibers.

27. A catheter for use in a medical procedure comprising:
a flexible elongate body defining a central axis and adapted to be introduced into a patient during said medical procedure and including a strain sensing assembly for repeated resolution of a computed magnitude and direction of a force vector exerted on a distal end of said flexible elongate body, said strain sensing assembly being proximate said distal end of said flexible elongate body, said computed direction of said force vector defining one of an oblique angle and a perpendicular angle relative said central axis, said strain sensing assembly including:
a deformable portion;
a plurality of fiber optic strain sensors affixed to said deformable portion, each of said fiber optic strain sensors comprising:
a tubular outer portion having a proximal end and a distal end;
a transmitting element affixed to said tubular outer portion at a contact location proximate said proximal end, said transmitting element having a free end that extends into said tubular outer portion; and
a reflecting element operatively coupled with said free end of said transmitting element to define a gap for interferometery, said gap having an operative length between said free end and said reflecting element, said operative length being variable and responsive to deformation of said deformable portion,
wherein said deformable portion, said tubular outer portion and said transmitting element have a substantially similar coefficient of thermal expansion in a direction parallel to said operative length so that said operative length remains within a predetermined range when said deformable portion of said elongate body is subject to a predetermined range of bulk temperature change.

28. The catheter of claim 27 further comprising:
one or more sources of electromagnetic radiation operatively coupled to each of said plurality of fiber optic strain sensors and transmitting electromagnetic radiation to each gap of said plurality of fiber optic strain sensors to form a plurality of interferometers, each of said interferometers outputting modulated waveforms, each waveform being characteristic of the corresponding of said operative lengths;
one or more receivers operatively coupled to said plurality of fiber optic strain sensors to detect said modulated waveforms; and
means operatively coupled to said one or more receivers for analyzing said modulated waveforms to infer at least one strain on said deformable portion of said elongate body.

29. The catheter of claim 28 further comprising means for resolving said force vector from said at least one strain, said force vector having at least one of an axial component and a transverse component.

30. The catheter of claim 28 wherein said plurality of interferometers are Fabry-Perot interferometers.

31. The catheter of claim 27 wherein a difference between said substantially similar coefficients of thermal expansion of said deformable portion and said transmitting element is within 2 μ/K.

* * * * *